(12) United States Patent
Foley

(10) Patent No.: US 12,215,120 B1
(45) Date of Patent: Feb. 4, 2025

(54) TERPENE O-GLYCOSIDES

(71) Applicant: P2 Science, Inc., Woodbridge, CT (US)

(72) Inventor: Patrick Foley, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/746,632

(22) Filed: May 17, 2022

Related U.S. Application Data

(60) Provisional application No. 63/189,546, filed on May 17, 2021.

(51) Int. Cl.
C07H 15/04 (2006.01)
C07H 1/00 (2006.01)

(52) U.S. Cl.
CPC ............. *C07H 15/04* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 2,020,298 A | 11/1935 | Carothers et al. |
| 3,335,053 A | 8/1967 | Guenther |
| 3,829,505 A | 8/1974 | Herold et al. |
| 3,980,697 A | 9/1976 | El-Chahawi et al. |
| 4,021,507 A | 5/1977 | Ford |
| 4,070,386 A | 1/1978 | Rossmy |
| 4,218,379 A | 8/1980 | Harris et al. |
| 4,366,270 A | 12/1982 | Rüter |
| 4,381,416 A | 4/1983 | Kyo et al. |
| 5,030,768 A | 7/1991 | Chen et al. |
| 5,264,547 A | 11/1993 | Yamaguchi et al. |
| 5,292,845 A | 3/1994 | Kawasaki |
| 5,531,910 A | 7/1996 | Severns et al. |
| 5,545,601 A | 8/1996 | Le-Khac |
| 5,562,847 A | 10/1996 | Waite et al. |
| 5,616,679 A | 4/1997 | Fies |
| 6,001,789 A | 12/1999 | Trinh et al. |
| 6,117,521 A | 9/2000 | Yoshida et al. |
| 6,348,618 B1 | 2/2002 | Anderson et al. |
| 6,355,845 B1 | 3/2002 | Clement et al. |
| 6,359,101 B1 | 3/2002 | O'Connor et al. |
| 6,369,025 B1 | 4/2002 | Trinh et al. |
| 7,355,066 B1 | 4/2008 | Johnson et al. |
| 7,445,790 B2 | 11/2008 | Oguchi et al. |
| 9,068,091 B2 | 6/2015 | Hofstra et al. |
| 9,982,073 B2 | 5/2018 | Ghandi et al. |
| 10,059,801 B2 | 8/2018 | Foley et al. |
| 10,844,169 B2 | 11/2020 | Foley et al. |
| 11,008,271 B2 | 5/2021 | Yang et al. |
| 11,518,850 B2 | 12/2022 | Foley et al. |
| 11,827,746 B2 | 11/2023 | Foley et al. |
| 11,872,300 B2 | 1/2024 | Foley et al. |
| 2004/0152830 A1 | 8/2004 | Kim et al. |
| 2004/0202689 A1 | 10/2004 | Subramanyan et al. |
| 2005/0256347 A1 | 11/2005 | Goebbel et al. |
| 2006/0018977 A1 | 1/2006 | Bruza et al. |
| 2008/0311066 A1 | 12/2008 | Samain et al. |
| 2012/0046244 A1 | 2/2012 | Rogers et al. |
| 2013/0202543 A1 | 8/2013 | Küper et al. |
| 2017/0057940 A1 | 3/2017 | Foley et al. |
| 2017/0088536 A1 | 3/2017 | Foley et al. |
| 2017/0283553 A1 | 10/2017 | Foley et al. |
| 2018/0071188 A1 | 3/2018 | Barhoum et al. |
| 2019/0184049 A1 | 6/2019 | Salaam-Zayid et al. |
| 2020/0179247 A1 | 6/2020 | Verdier et al. |
| 2020/0392287 A1 | 12/2020 | Foley et al. |

FOREIGN PATENT DOCUMENTS

| | | | |
|---|---|---|---|
| CN | 104304728 A | | 1/2015 |
| DE | 10 2005 025 739 A1 | | 12/2006 |
| JP | 2006-273796 A | | 10/2006 |
| JP | 2008-050415 A | | 3/2008 |
| JP | 2019005262 A | * | 1/2019 |
| JP | 2020152663 A | * | 9/2020 |
| WO | WO 2006/057086 | | 6/2006 |
| WO | WO 2016/033437 A2 | | 3/2016 |
| WO | WO 2016/096792 | | 6/2016 |
| WO | WO 2019/028053 A1 | | 2/2019 |
| WO | WO 2019/059375 | | 3/2019 |

OTHER PUBLICATIONS

Kato et al., Journal of Colloid and Interface Science, 2007, 213(1), pp. 122-129 (Year: 2007).*
AN 2019:108781 as it relates to JP 2019005262. (Year: 2019).*
AN 2020:1893458 as it relates to JP 2020152663. (Year: 2020).*
Désaubry, et al., "Toward Higher Polyprenols Under 'Prebiotic' Conditions," *Tetrahedron Letters*, Issue 44, pp. 6959-6961, (2003); DOI: 10.1016/S0040-4039(03)01624-1.
Halbert, S., "Plant-derived compounds and extracts with potential as aphid repellents", *Ann Appl Biol.*, 154(2), pp. 303-307, (2009).
Hanson, "Chiral Acylic Synthetic Intermediates from Readily Available Monoterpenoids," *Journal of Chemical Research*, vol. 39, pp. 617-621, (2015).
Marchal et al., "Lyotropic liquid crystal behaviour of azelate and succinate monoester surfactants based on fragrance alcohols", *Journal of Colloid and Interface Science*, vol. 321, pp. 177-185, (2008).
Nagai, "The Formation of Ethers from dl-Citronellol in the Presence of Boron Trifluoride Etherate," *Bulletin of the Chemical Society of Japan*, vol. 49, No. 1, pp. 265-269, (1976).
Nagai, et al., "The Formation of Ethers from Unsaturated Aliphatic Alcohols in the Presence of Boron Trifluoride Etherate," *Bulletin of the Chemical Society of Japan*, vol. 51, No. 11, pp. 3273-3276, (1978).
PubChem CID 13469549, 11 pages, (2007); retrieved on Sep. 10, 2018 from http://pubchem.ncbi.nlm.nih.gov/compound/013469549#section=Top>.

(Continued)

Primary Examiner — Traviss C McIntosh, III
(74) Attorney, Agent, or Firm — Hoxie & Associates LLC

(57) ABSTRACT

The present disclosure is directed to novel glycoside derivatives of terpenes, particularly derivatives of terpene alcohols, and methods of making them, compositions comprising them, and methods for using them.

23 Claims, No Drawings

(56) References Cited

OTHER PUBLICATIONS

PubChem, OPEN Chemistry Database, PubChem CID 8892, pp. 4, (2004), 60 pages.
PubChem, OPEN Chemistry Database, PubChem SID 105168722, PubChem CID 112049, (2011), 7 pages.
PubChem, OPEN Chemistry Database, PubChem SID 355155508, PubChem CID 114416, (2018), 6 pages.
PubChem, OPEN Chemistry Database, PubChem CID 11172890, (2006), 10 pages.
PubChem, OPEN Chemistry Database, PubChem CID 23297377, (2007), 9 pages.
Salkar et al., "Alkylglucosides with isoprenoid-type hydrophobic chains-effects of hydrophobic chain size on the aqueous phase behavior", *Chemistry and Physics of Lipids*, vol. 127, pp. 65-75, (2004).
Takahashi, et al., "Cationic Polymerization Behavior of Alkoxyallenes," *Macromolecules*, vol. 28, No. 4, pp. 866-869, (1995).
Wheeler et al. "2,3-Dihydrofarnesyl and citronellyl esters in the paracloacal gland secretions of the brown caiman (*Caiman crocodilus fuscus*) from Costa Rica", *Biochemical Systematics and Ecology*, vol. 27, pp. 27-32, (1998).
Worzakowska, "Synthesis, Characterization, and Thermal Properties of New Flavor Compounds," *J Therm Anal Calorim*, vol. 116, pp. 727-736, (2014); DOI: 10.1007/s10973-013-3541-1.
Worzakowska, "Thermal Properties of Neryl Long-Chain Esters Obtained Under Microwave Irradiation," *J Therm Anal Calorim*, vol. 120, pp. 1715-1722, (2015); DOI: 10.1007/s10973.015-4489-0.
Yamashita et al., "Small angle X-ray scattering from lamellar phase for -3,7-dimethyloctylglucoside/water system: comparison with -n-alkylglucosides", *Colloids and Surfaces A: Physicochem. Eng. Aspects*, vol. 250, pp. 485-490, (2004).
Kegel et al., "Alkyl melibioside and alkyl cellobioside surfactants: effect of sugar headgroup and alkyl chain length on performance," *Green Chemistry*, 16 (2016) (Abstract Only).
Paroul, et al., "Solvent-Free Production of Bioflavors by Enzymatic Esterification of Citronella (*Cymbopogon winterianus*) Essential Oil", Applied Biochemistry and Biotechnology, 166: 13-21 (2012).
Rashid, A., et al., "Enzymatic Synthesis of Citronellyl Palmitate in Organic Media: Process Optimization and Kinetic Evaluation", Asian Journal of Chemistry, 28(2): 298-300 (2016).
Swift, K., "Catalytic Transformations of the Major Terpene Feedstocks", Topics in Catalysis, 27(1-4): 143-155 (2004).

* cited by examiner

TERPENE O-GLYCOSIDES

CROSS-REFERENCE TO RELATED APPLICATIONS

This application is U.S. nonprovisional application which claims priority to, and the benefit of, U.S. Provisional Application No. 63/189,546, filed on May 17, 2021, the contents of which are hereby incorporated by reference in its entirety.

FIELD OF INVENTION

The present disclosure is directed to novel glycoside derivatives of terpenes, particularly derivatives of terpene alcohols, and methods of making them, compositions comprising them, and methods for using them.

BACKGROUND

Terpenes and terpene derivatives constitute one of the most diverse, commercially sought after, and industrially important classes of natural products. Terpenes occur in all organisms and are particularly prevalent in plants, from which they are industrially isolated. The ready commercial access and low-cost of terpenes continually drives innovation into their chemical derivatization which find use in polymer science, the flavor & fragrance industry, the cosmetic industry, the pharmaceutical industry, and as surfactants, plastic additives, and other industrial uses.

While base terpenes are inexpensive and widely available ($C_{5n}H_{8n}$ derivatives, n=1, 2, 3, etc.), chemically functionalized terpenes (terpenoids) are more useful, especially terpene alcohols. Common monoterpene alcohols include the following:

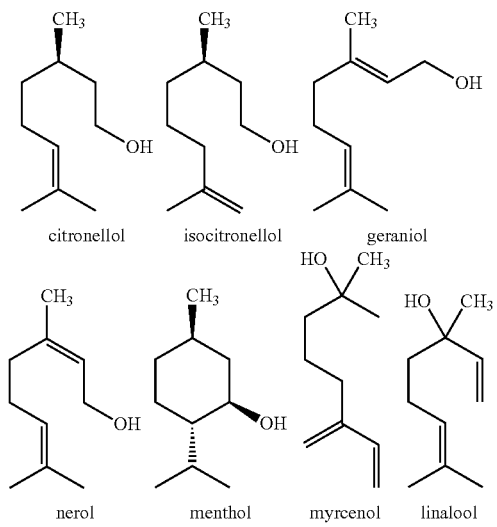

citronellol, isocitronellol, geraniol, nerol, menthol, myrcenol, linalool

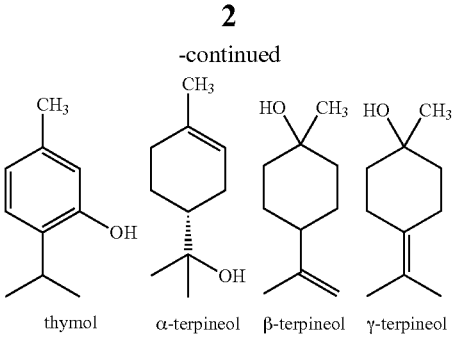

thymol, α-terpineol, β-terpineol, γ-terpineol

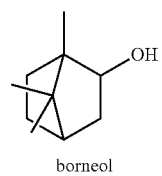

borneol

In addition to monoterpene alcohols, there are also inexpensive and widely available sesquiterpene alcohols, such as:

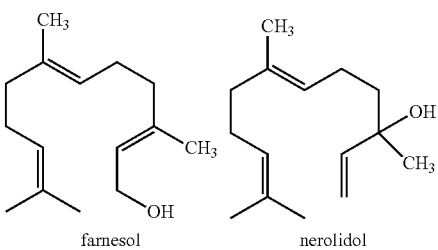

farnesol, nerolidol

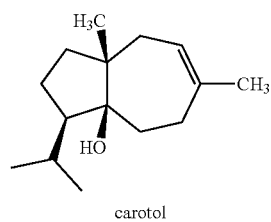

carotol

Terpene alcohol derivatives also include polymers and oligomers of terpene alcohols. For example, citronellol has been formed into useful oligomeric and polymeric products having the following structure:

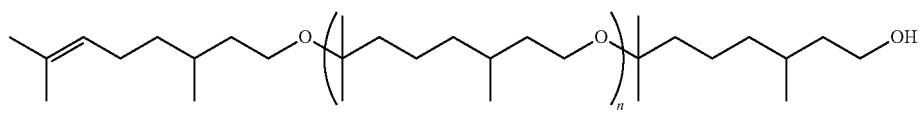

wherein n: 0-20 (e.g., 0-3). Dimers, trimers, and other oligomers of citronellol have been described. See, e.g., US2017/0283553, US2020/0165383, and US2020/0392287, the contents of each of which are hereby incorporated by reference in their entireties.

Glycosides, such as glucosides, are widespread in nature and fulfill numerous biological roles. Non-natural, synthetic glycosides have become increasingly important in industry because of the ability to fine tune the chemical and physical properties of the glycosides by careful selection of the glycoside core, the nature of the glycosidic linkage or linkages, and the nature and extent of ether formation on the glycoside core. These compounds find a variety of uses, for example, as surfactants, emulsifiers, emollients, lubricants, defoamers, adjuvants and others. These compounds are commonly found in personal care and cosmetic compositions. One of the most appealing features of these compounds is the biodegradability of the glycosidic linkages, which ensures that these compounds are generally safe for the environment and nonpersistent.

There remains a need for new compounds in this field, with new or different properties, such as improved stability, improved biodegradability, or improved environmental impact. It would be especially advantageous to have new glycoside ethers sourced from renewable resources.

BRIEF SUMMARY OF THE INVENTION

The present disclosure provides terpene alcohol O-glycoside ethers, derived from terpene alcohols, and oligomers and derivatives thereof, and glucose and other saccharides (including oligosaccharides), such as maltose. These compounds are useful in numerous types of compositions, and numerous roles. For example, these compounds may be used as emollients, lubricants, defoamers, adjuvants and other uses, and are especially useful as ingredients in personal care compositions and cosmetic compositions.

In a second aspect, the present disclosure provides a method of preparing such compounds.

In a third aspect, the present disclosure provides compositions and products comprising such compounds. In some embodiments, said compounds are useful in a variety of applications, including as or in cosmetics, soaps, hair care products, fragrances, sunscreens, plastic additives, paints, coatings, lubricants, and surfactants.

DETAILED DESCRIPTION OF THE INVENTION

As used herein, the term "terpene alcohol" refers to a naturally terpene or terpenoid having or modified to have at least one alcohol functionality. The term includes both naturally occurring terpene alcohols, and alcohols derived from naturally occurring terpenes, such as by double bond oxidation, ketone reduction, or the like. As used herein, the term "terpene derivative" or "terpene alcohol derivatives" includes saturated and partially saturated derivatives of terpenes and terpene alcohols. Terpenes, terpene alcohols and other terpenoids commonly have 1, 2, 3 or more double bonds. In a saturated derivative all double bonds are hydrogenated, while in a partially saturated derivative, at least one double bond is hydrogenated, but at least one double bond is not. In this context, the double bonds of an aromatic ring are included; thus, a benzene ring can be considered to be partially saturated to form a cyclohexadiene or a cyclohexene ring, or fully saturated to form a cyclohexane ring.

In a first aspect, the present disclosure provides Compound 1, a terpene alcohol O-glycoside ether compound of the general formula (I):

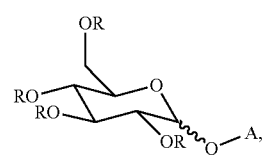

Formula (I)

in free or salt form; or
a terpene alcohol (1→6)-O-glycoside ether compound of the general formula (II):

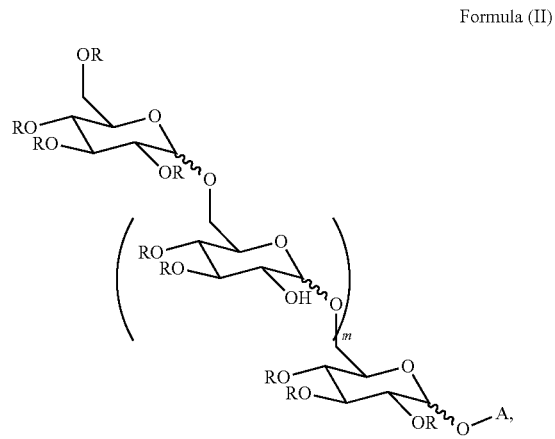

Formula (II)

in free or salt form, wherein m is an integer from 0-10; or
a terpene alcohol (1→4)-O-glycoside ether compound of the general formula (III):

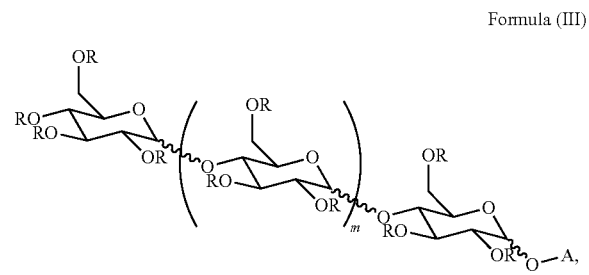

Formula (III)

in free or salt form, wherein m is an integer from 0-10; wherein in each of Formula (I) and Formula (II) and Formula (III):
A is the core of a terpene alcohol or derivative thereof; and
each R is independently selected from H, $C_{1-6}$alkyl (e.g., methyl), and —(CO)—$C_{1-6}$alkyl (e.g., acetyl); or
each R is independently optionally a unit B, wherein B is the core of a terpene alcohol or derivative thereof which is the same or different than A.

In a preferred embodiment, the product compound of Formula I is an isodecyl glycoside (i.e., group A and/or group B is an isodecyl group).

While the drawings of the compounds of Formula I, Formula II, and Formula III used herein reflect the stereochemical arrangement of glycosides wherein each unit is a glucoside unit, it is understood that the scope of the present invention applies to all other isomeric glycosides as well, for example, to glycosides wherein one or more of the glycoside monomeric units are based on the other aldohexoses (e.g., allose, altrose, mannose, gulose, idose, galactose or talose), or based on the ketohexoses (e.g., psicose, fructose, sorbose, tagatose). Thus, merely as an example, the present disclosure also embraces a compound of Formula I, wherein the compound has the following structure, which has the stereochemistry of a galactoside:

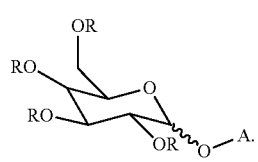

Formula (Ib)

Corresponding drawings can be made for the compounds of Formula II and III, wherein any one or more of the glucoside units is replaced by a galactoside unit (or any other aldohexoside unit). Similarly, it is understood that if any such glycoside unit is based on a ketohexose, the glycoside unit may adopt a furanose structure, rather than the pyranose structure common to aldohexoses. As such, for example, the compound of Formula I can be a compound having a structure as follows (which is a fructoside):

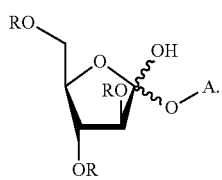

Formula (Ic)

Therefore, in the compounds of Formula I, II, and III, it is understood that the stereochemistry shown at the asymmetric C-2, C-3, C-4, C-5 carbon atoms (as numbered below) is representative of an embodiment of the disclosure, and other stereochemical combinations are permissible.

As used herein, it is understood that each carbon atom of a glycoside or glucoside unit is numbered as follows:

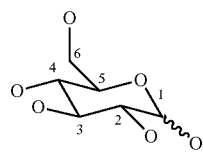 [SMILES: OCC1OC(O)C(O)C(O)C1O]

As used herein, it is also understood that the C—O bond of the number 1 carbon of each glycoside or glucoside unit (the glycosidic carbon) can be oriented either below the plane of the ring (an α glycosidic linkage) or above the plane of the ring (a β glycosidic linkage), as shown below:

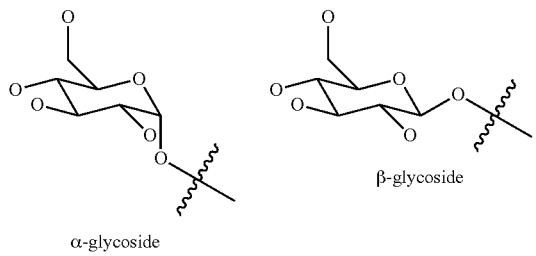 [SMILES: *OC1OC(CO)C(O)C(O)C1O ; *OC1OC(CO)C(O)C(O)C1O]

α-glycoside    β-glycoside

It is understood that in the phrases "A is the core of a terpene alcohol or derivative thereof," and "B is the core of a terpene alcohol or derivative thereof," that the terpene alcohol, or derivative thereof, from which the compound of Formula I or II or III is derived has the formula A—OH or B—OH. Thus, the ether functional groups of the compounds of Formula I and II and III are formed, or are formable by, condensation reactions between the glycone hydroxyl groups and the terpene alcohols, for example, as follows:

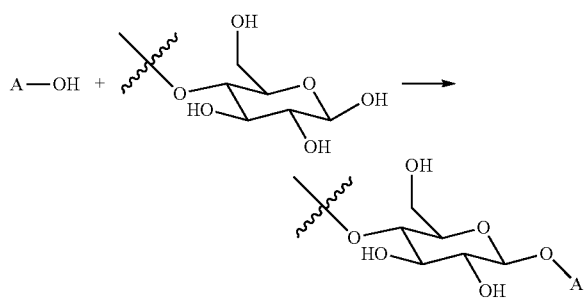

In further embodiments of the first aspect, the present disclosure provides as follows:

1.1 Compound 1, wherein the compound is the terpene O-glycoside ether compound of the general formula (I).
1.2 Compound 1, wherein the compound is the terpene alcohol (1→6)-O-glycoside ether compound of the general formula (II).
1.3 Compound 1, wherein the compound is the terpene alcohol (1→4)-O-glycoside ether compound of the general formula (III).
1.4 Compound 1.2 or 1.3, wherein m is 0.
1.5 Compound 1.2 or 1.3, wherein m is selected from 1, 2, 3, 4, 5, or 6 (e.g., m is 1 or 2).
1.6 Compound 1, or any of 1.1-1.5, wherein A is the core of a terpene alcohol, or derivative thereof, wherein said terpene is a monoterpene, sesquiterpene, diterpene, sesterterpene, or triterpene.
1.7 Compound 1, or any of 1.1-1.5, wherein A is the core of a terpene alcohol, or derivative thereof, wherein said terpene is a monoterpene or sesquiterpene.
1.8 Compound 1, or any of 1.1-1.5, wherein A is the core of a terpene alcohol, or derivative thereof, wherein said terpene is a monoterpene (e.g., A is an isodecyl moiety).
1.9 Compound 1, or any of 1.1-1.5, wherein A is the core of a terpene alcohol, or derivative thereof, wherein said terpene alcohol is selected from citronellol, isocitronellol, geraniol, nerol, menthol, myrcenol, linalool, thymol, α-terpineol, β-terpineol, γ-terpineol, borneol, farnesol, nerolidol, and carotol.

1.10 Compound 1.9, wherein said terpene alcohol is selected from citronellol, geraniol, nerol, myrcenol, linalool, and farnesol.

1.11 Compound 1.10, wherein said terpene alcohol is selected from citronellol, myrcenol, linalool, and farnesol.

1.12 Compound 1, or any of 1.1-1.5, wherein A is the core of a terpene alcohol, or derivative thereof, wherein said terpene alcohol, or derivative, is an oligomer of citronellol.

1.13 Compound 1 or any of 1.1-1.12, wherein said terpene alcohol, or derivative thereof, has its natural unsaturation.

1.14 Compound 1 or any of 1.1-1.12, wherein said terpene alcohol, or derivative thereof, is partially unsaturated (e.g., monounsaturated or diunsaturated).

1.15 Compound 1 or any of 1.1-1.12, wherein said terpene alcohol, or derivative thereof, is fully saturated (e.g., said terpene alcohol is a fully saturated monoterpene derivative, e.g., an isodecyl moiety).

1.16 Compound 1, or any of 1.1-1.5, wherein A is selected from the group consisting of:

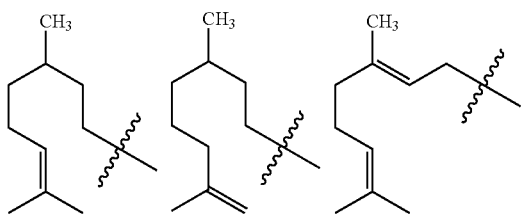

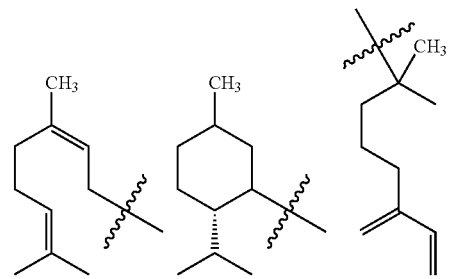

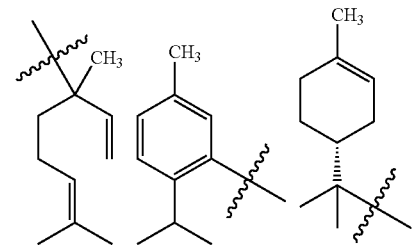

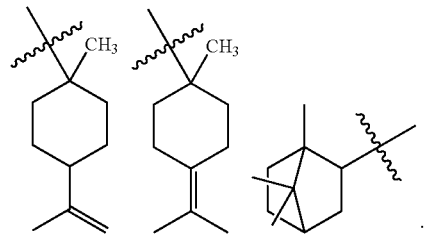

1.17 Compound 1, or any of 1.1-1.5, wherein A is selected from the group consisting of:

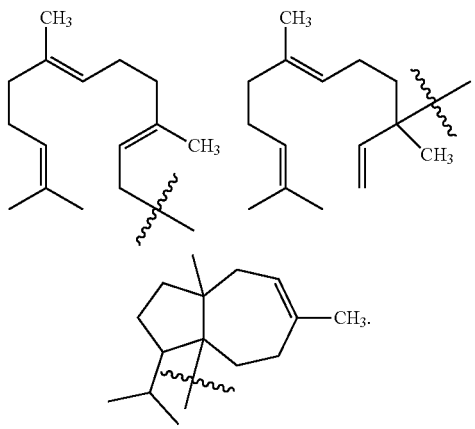

1.18 Compound 1, or any of 1.1-1.5, wherein A is selected from the group consisting of:

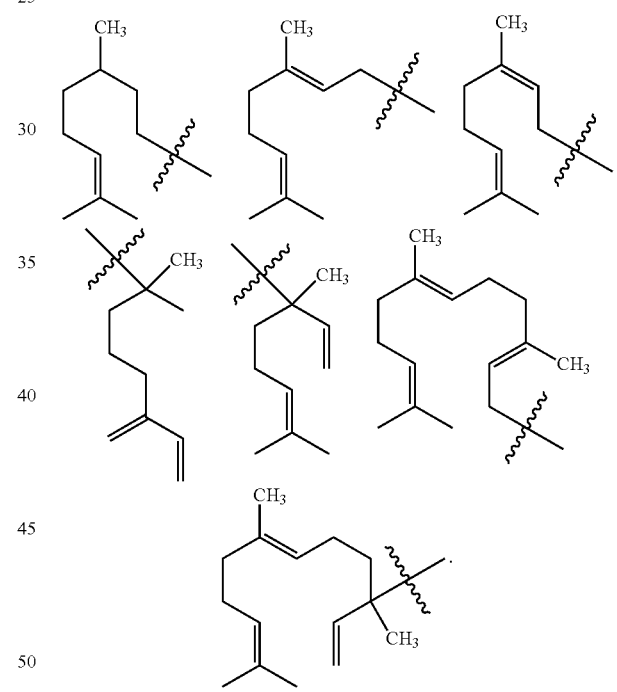

1.19 Compound 1, or any of 1.1-1.5, wherein A is selected from the group consisting of:

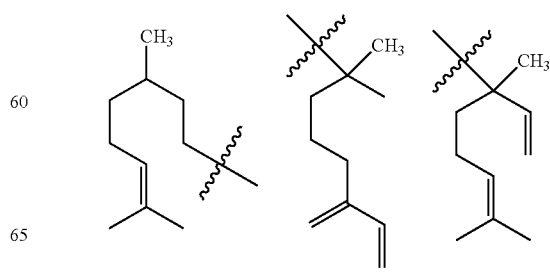

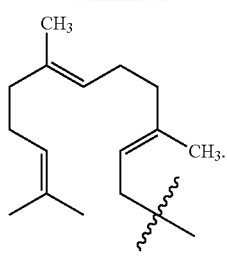
1.20 Compound 1, or any of 1.1-1.5, wherein A is:
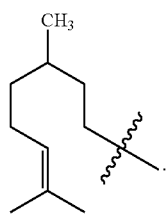 [SMILES: *CCC(C)CCC=C(C)C]
1.21 Compound 1, or any of 1.1-1.5, wherein A is selected from the group consisting of:
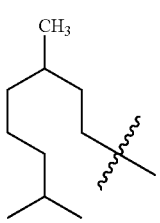 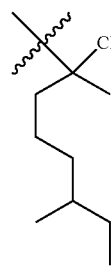 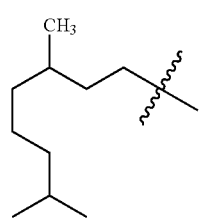
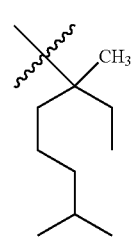 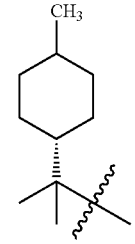 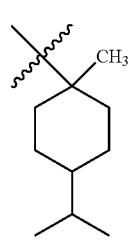
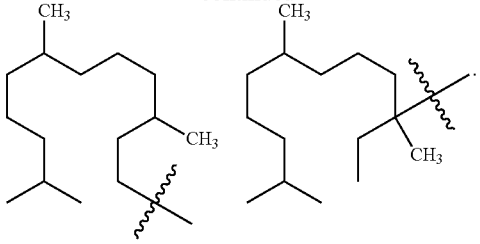
1.22 Compound 1, or any of 1.1-1.5, wherein A is selected from the group consisting of:
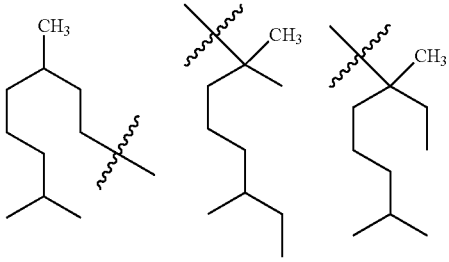
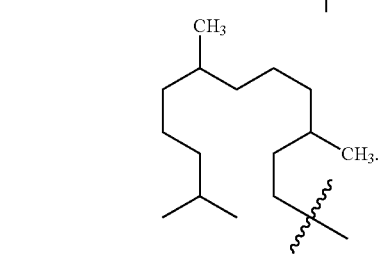
1.23 Compound 1, or any of 1.1-1.5, wherein A is:
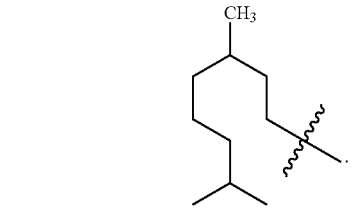 [SMILES: *CCC(C)CCCC(C)C]
1.24 Compound 1, or any of 1.1-1.5, wherein A is:
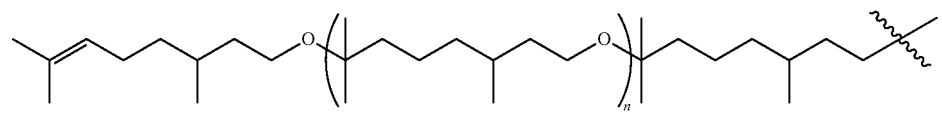

wherein n is an integer from 0-20 (e.g., 0-3, 0, 1 or 2).
1.25 Compound 1, or any of 1.1-1.5, wherein A is:

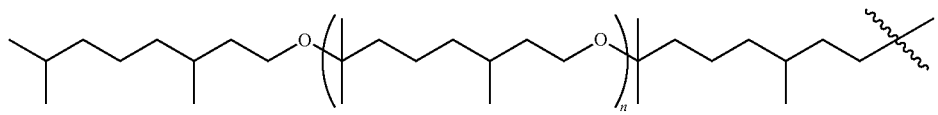

wherein n is an integer from 0-20 (e.g., 0-3, 0, 1 or 2).
1.26 Compound 1, or any of 1.1-1.25, wherein all substituents R are selected from H, $C_{1-6}$alkyl (e.g., methyl), and —(CO)—$C_{1-6}$alkyl (e.g., acetyl).
1.27 Compound 1.26, wherein all substituents R are H.
1.28 Compound 1.26, wherein at least half of the substituents R are H, and the other substituents R are $C_{1-6}$alkyl (e.g., methyl) or —(CO)—$C_{1-6}$alkyl (e.g., acetyl).
1.29 Compound 1, or any of 1.1-1.25, wherein one substituent R in the compound is a unit B, and all other substituents R are selected from H, $C_{1-6}$alkyl (e.g., methyl), and —(CO)—$C_{1-6}$alkyl (e.g., acetyl).
1.30 Compound 1.29, wherein the one substituent R which is a unit B is on the terminal glucose unit of the oligomer of Formula (II) or (III) (i.e., the glucose unit farthest from substituent A), optionally wherein each of said units B are the same unit B.
1.31 Compound 1, or any of 1.1-1.25, wherein one substituent R on each glucose unit is a unit B, and all other substituents R are selected from H, $C_{1-6}$alkyl (e.g., methyl), and —(CO)—$C_{1-6}$alkyl (e.g., acetyl).
1.32 Any one of compounds 1.29-1.31, wherein the substituent or substituents R which are a unit B, are the substituent or substituents R located on the 6-carbon hydroxy group of the glucose unit or units.
1.33 Any one of compounds 1.29-1.31, wherein the substituent or substituents R which are a unit B, are the substituent or substituents R located on the 4-carbon hydroxy group of the glucose unit or units.
1.34 Any one of compounds 1.29-1.31, wherein all other substituents R (which are not units B) are H.
1.35 Any one of compounds of 1.39-1.34, wherein the unit or units B are each the core of a terpene alcohol, or derivative thereof, wherein said terpene is a monoterpene, sesquiterpene, diterpene, sesterterpene, or triterpene.
1.36 Compound 1.35, wherein B is the core of a terpene alcohol, or derivative thereof, wherein said terpene is a monoterpene or sesquiterpene.
1.37 Compound 1.35, wherein B is the core of a terpene alcohol, or derivative thereof, wherein said terpene is a monoterpene (e.g., A is an isodecyl moiety).
1.38 Compound 1.35, wherein B is the core of a terpene alcohol, or derivative thereof, wherein said terpene alcohol is selected from citronellol, isocitronellol, geraniol, nerol, menthol, myrcenol, linalool, thymol, α-terpineol, β-terpineol, γ-terpineol, borneol, farnesol, nerolidol, and carotol.
1.39 Compound 1.38, wherein said terpene alcohol is selected from citronellol, geraniol, nerol, myrcenol, linalool, and farnesol.
1.40 Compound 1.39, wherein said terpene alcohol is selected from citronellol, myrcenol, linalool, and farnesol.
1.41 Compound 1.35, wherein B is the core of a terpene alcohol, or derivative thereof, wherein said terpene alcohol, or derivative, is an oligomer of citronellol.
1.42 Any one of compounds of 1.29-1.41, wherein said terpene alcohol, or derivative thereof, has its natural unsaturation.
1.43 Any one of compounds of 1.29-1.41, wherein said terpene alcohol, or derivative thereof, is partially unsaturated (e.g., monounsaturated or diunsaturated).
1.44 Any one of compounds of 1.29-1.41, wherein said terpene alcohol, or derivative thereof, is fully saturated (e.g., said terpene alcohol is a fully saturated monoterpene derivative, e.g., an isodecyl moiety).
1.45 Compound 1.35, wherein B is selected from the group consisting of:

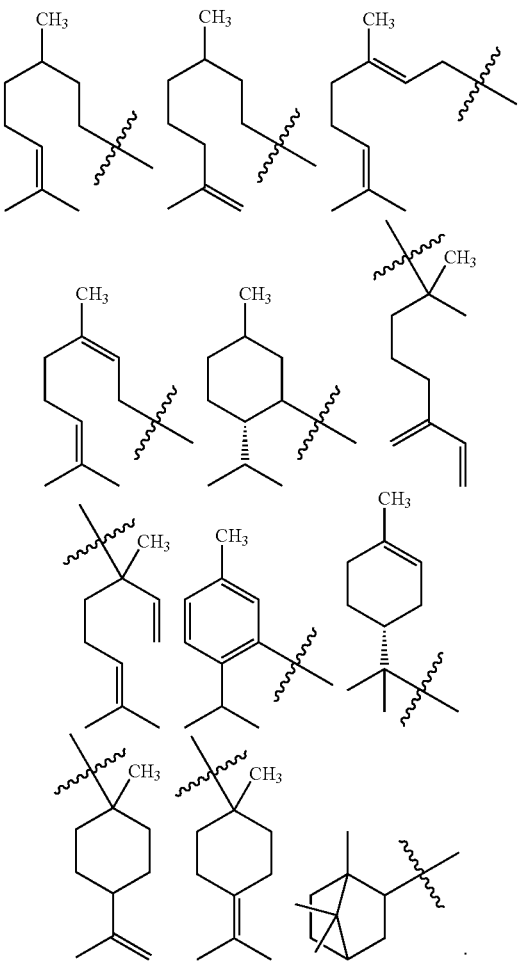

1.46 Compound 1.35, wherein B is selected from the group consisting of:
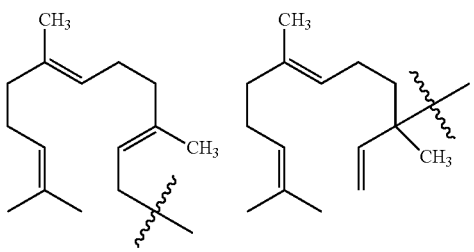
1.47 Compound 1.35, wherein B is selected from the group consisting of:
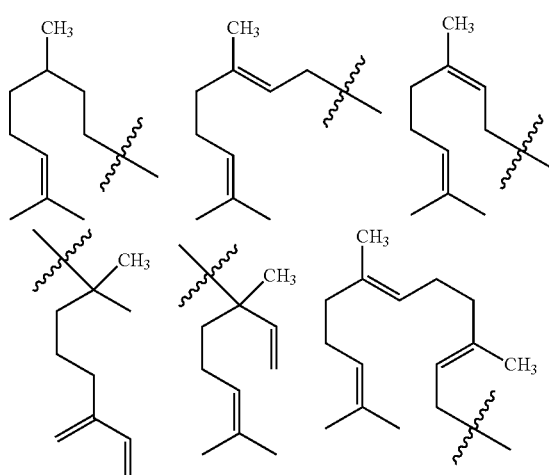
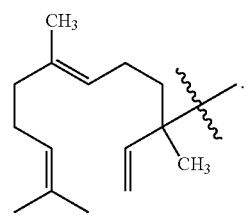
1.48 Compound 1.35, wherein B is selected from the group consisting of:
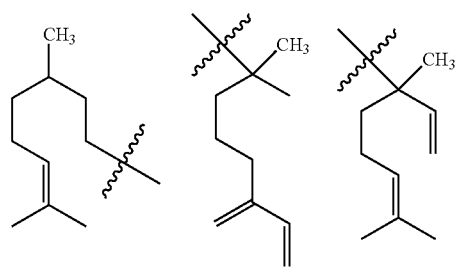
-continued
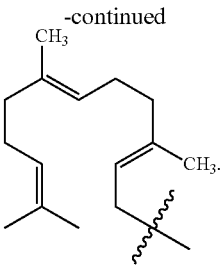
1.49 Compound 1.35, wherein B is:
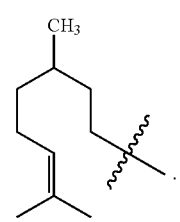 [SMILES: *CCC(C)CCC=C(C)C]
1.50 Compound 1.35, wherein B is selected from the group consisting of:
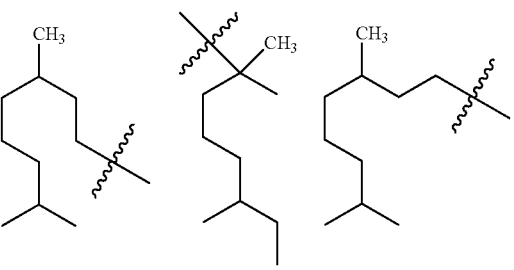
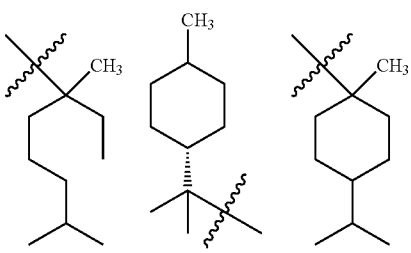
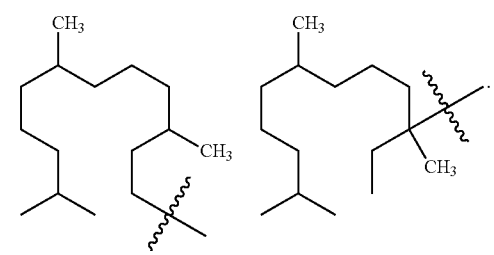

1.51 Compound 1.35, wherein B is selected from the group consisting of:

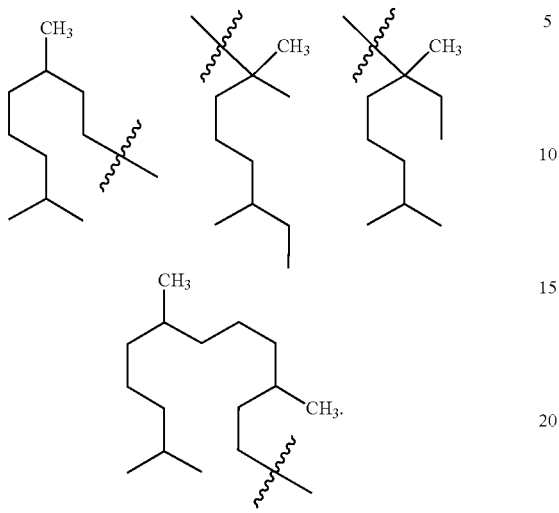

1.52 Compound 1.35, wherein B is:

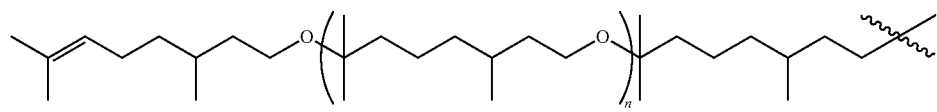

wherein n is an integer from 0-20 (e.g., 0-3, 0, 1 or 2).

1.53 Compound 1.35, wherein B is:

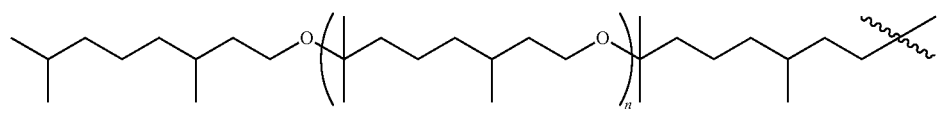

wherein n is an integer from 0-20 (e.g., 0-3, 0, 1 or 2).

1.54 Compound 1, or any of 1.1-1.53, wherein group A is an isodecyl group, e.g., selected from 2,4-dimethyloctan-2-yl, 2,6-dimethyl-octan-1-yl, 2,6-dimethyloctan-2-yl, 3,7-dimethyloctan-1-yl, and 3,7-dimethyloctan-3-yl.

1.55 Compound 1, or any of 1.1-1.54, wherein group B is an isodecyl group, e.g., selected from 2,4-dimethyloctan-2-yl, 2,6-dimethyl-octan-1-yl, 2,6-dimethyloctan-2-yl, 3,7-dimethyloctan-1-yl, and 3,7-dimethyloctan-3-yl.

1.56 Compound 1, or any of 1.1-1.55, wherein the compound is a compound of Formula I selected from the group consisting of:

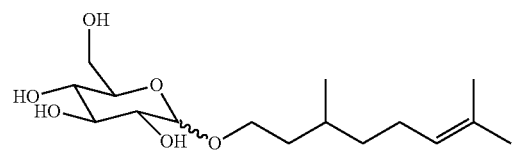

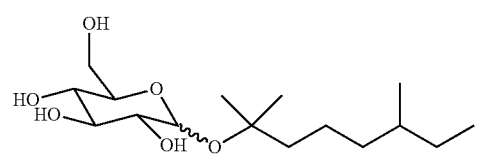

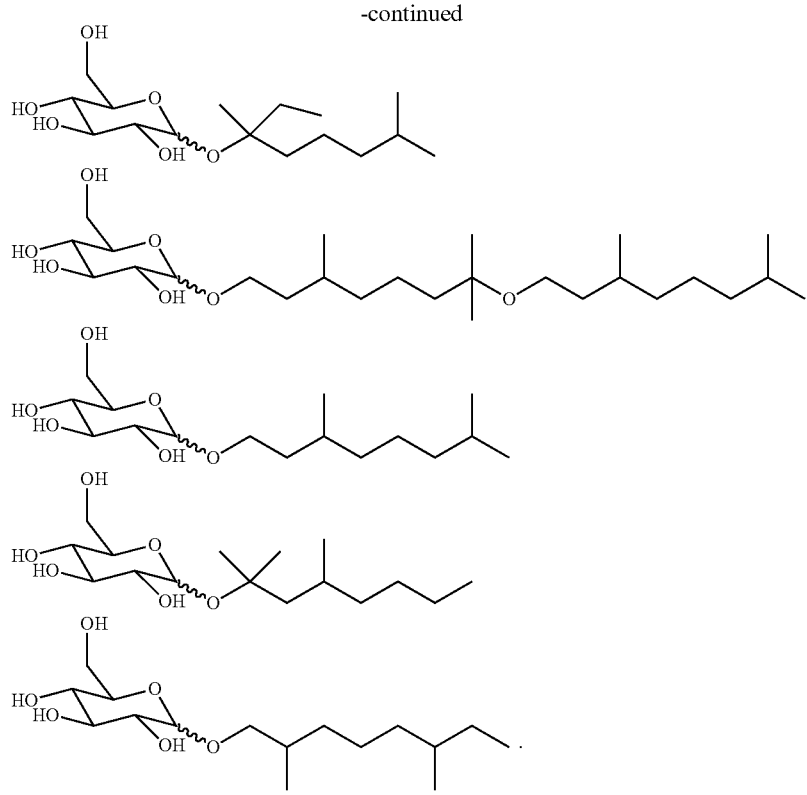
1.57 Compound 1, or any of 1.1-1.55, wherein the compound is a compound of Formula I selected from the group consisting of:
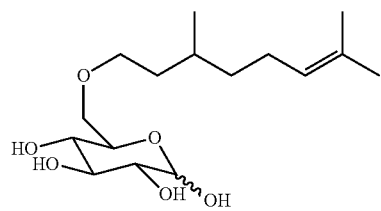
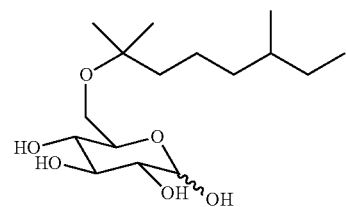
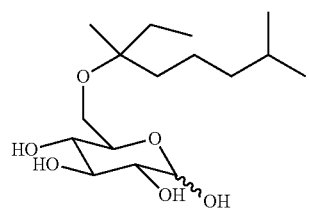
-continued
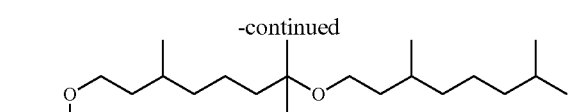
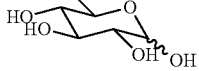
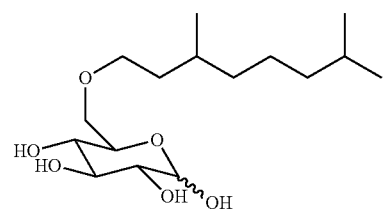
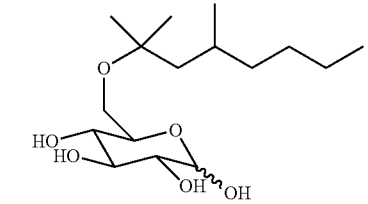

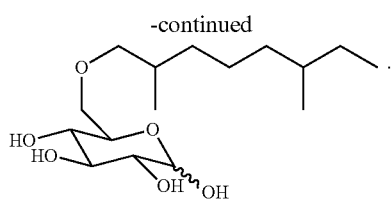

1.58 Compound 1, or any of 1.1-1.55, wherein the compound is a compound of Formula II having the formula:

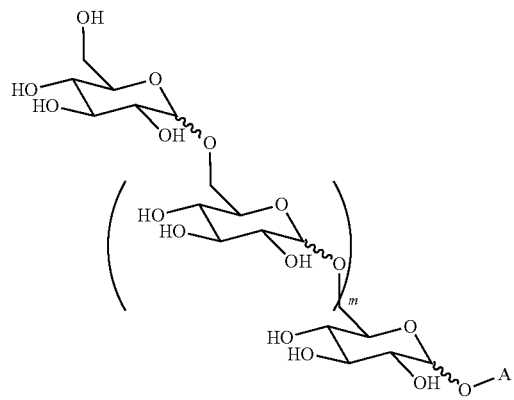

and wherein A is selected from the group consisting of:

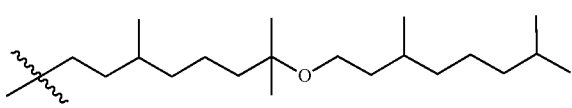

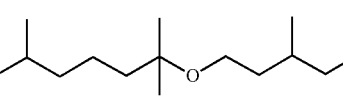

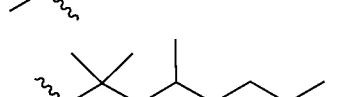

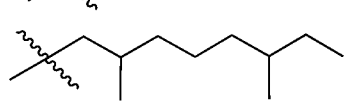

1.59 Compound 1, or any of 1.1-1.53, wherein the compound is a compound of Formula III having the formula:

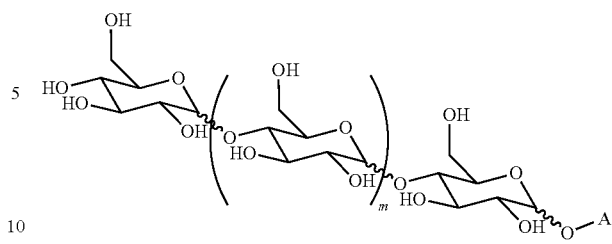

and wherein A is selected from the group consisting of:

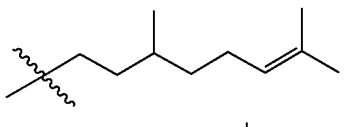

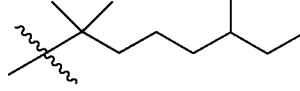

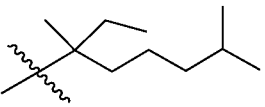

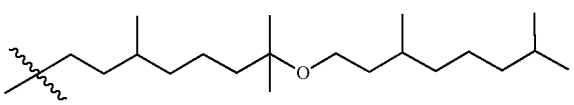

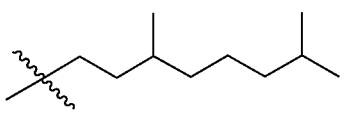

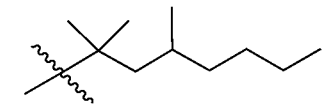

1.60 Compound 1, or any of 1.1-1.55, wherein the compound is a compound of Formula II having the formula:

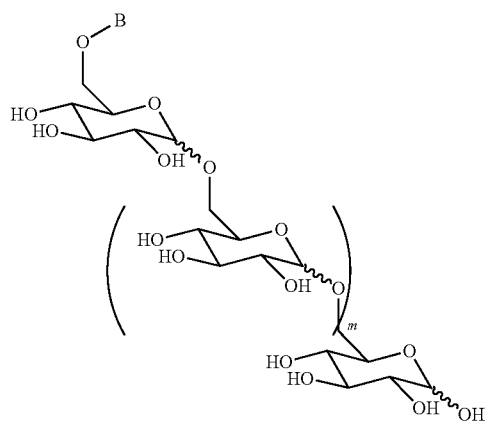

and wherein B is selected from the group consisting of:

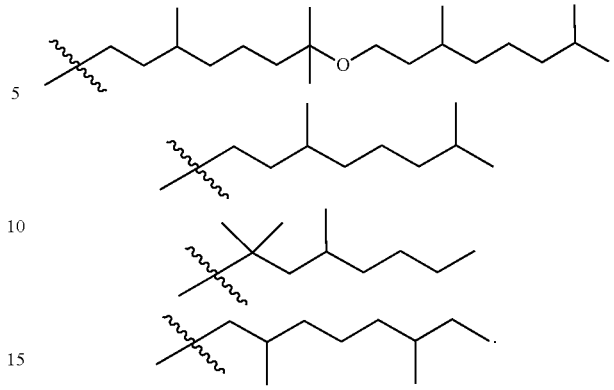

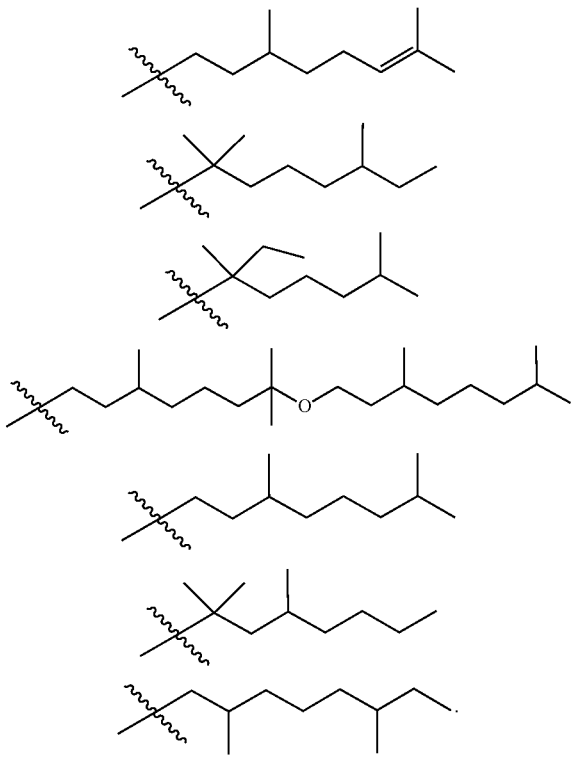

1.61 Compound 1, or any of 1.1-1.55, wherein the compound is a compound of Formula III having the formula:

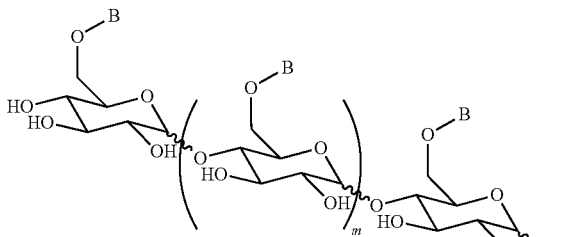

and wherein each B is H or is selected from the group consisting of:

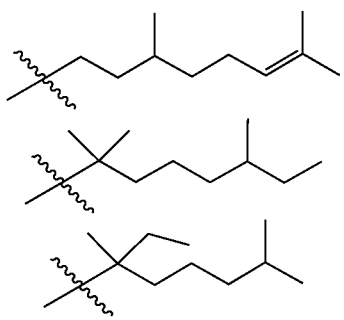

1.62 Any compounds 1.1-1.61, wherein the compound has a single stereogenic center within the substituent A, and each of any substituents B, and those centers have the R configuration.

1.63 Any compounds 1.1-1.61, wherein the compound has a single stereogenic center within the substituent A, and each of any substituents B, and those centers have the S configuration.

1.64 Any compounds 1.1-1.61, wherein the compound has two or three stereogenic centers within the substituent A, and each of any substituents B, and those centers all have the R configuration.

1.65 Any compounds 1.1-1.61, wherein the compound has two or three stereogenic centers within the substituent A, and each of any substituents B, and those centers all have the S configuration.

1.66 Compound 1, or any of 1.1-1.65, wherein the glucoside unit of the compound of Formula I, or any one or more of the glucoside units of the compounds of Formula II or III is replaced by an alternative glycoside unit, for example, selected from another aldohexose (e.g., allose, altrose, mannose, gulose, idose, galactose or talose), wherein in all of the other features of the structure are as provided in Compound 1 or any of 1.1-1.65.

1.67 Compound 1, or any of 1.1-1.65, wherein the glucoside unit of the compound of Formula I, or any one or more of the glucoside units of the compounds of Formula II or III is replaced by an alternative glycoside unit, for example, selected from a ketohexose (e.g., psicose, fructose, sorbose, tagatose), wherein in all of the other features of the structure are as provided in Compound 1 or any of 1.1-1.65, except that the ketohexose may be drawn as a furanose ring.

1.68 Compound 1, or any of 1.1-1.67, wherein the compound has a refractive index from 1.35 to 1.55, e.g., 1.40 to 1.50, or 1.42 to 1.48, or 1.43 to 1.46, or 1.44-1.45.

1.69 Compound 1, or any of 1.1-1.68, wherein the compound has a surface tension of 15 to 35 mN/m, e.g., 20 to 30 mN/m, or 22 to 28 mN/m, or 23 to 27 mN/m, or 24 to 26 mN/m, or about 25 mN/m.

In another embodiment of the first aspect, the present disclosure provides Compound 2, a terpene alcohol (1→6)-O-glycoside ether compound of the general formula (II-P):

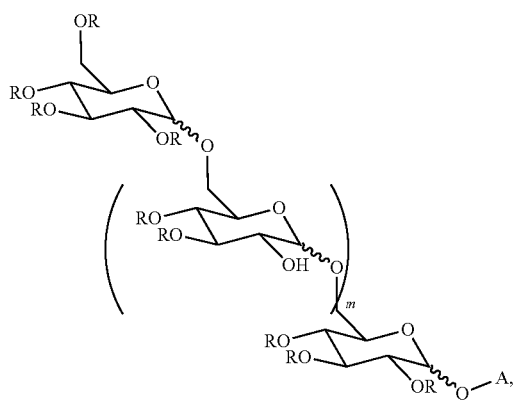

Formula (II-P)

in free or salt form, wherein m is an integer greater than 10; or a terpene alcohol (1→4)-O-glycoside ether compound of the general formula (III-P):

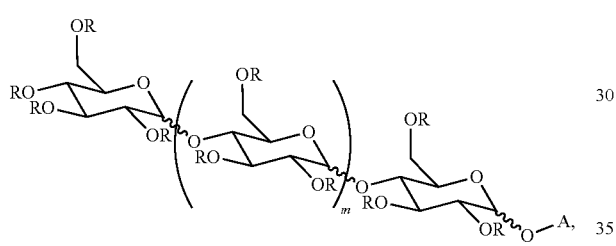

Formula (III-P)

in free or salt form, wherein m is an integer greater than 10; wherein in each of Formula (II-P) and Formula (III-P):

A is the core of a terpene alcohol or derivative thereof; and each R is independently selected from H, $C_{1-6}$alkyl (e.g., methyl), and —(CO)—$C_{1-6}$alkyl (e.g., acetyl); or each R is independently optionally a unit B, wherein B is the core of a terpene alcohol or derivative thereof which is the same or different than A.

In further embodiments of the first aspect, the present disclosure provides as follows:

2.1 Compound 2, wherein the compound is the terpene alcohol (1→6)-O-glycoside ether compound of the general formula (II-P).

2.2 Compound 2, wherein the compound is the terpene alcohol (1→4)-O-glycoside ether compound of the general formula (III-P).

2.3 Compound 2.1 or 2.2, wherein m is greater than 100, e.g., greater than 500, or greater than 1000 or greater than 5000, or greater than 10,000, or greater than 15,000, or greater than 20,000, or greater than 25,000, or greater than 30,000.

2.4 Compound 2, or any of 2.1-2.3, wherein the compound has a molecular weight (number average or weight average) of 100,000 to 10,000,000, e.g., 500,000 to 5,000,000.

2.5 Compound 2, or any of 2.1-2.4, wherein the compound is a modified cellulose.

2.6 Compound 2, or any of 2.1-2.5, wherein A is the core of a terpene alcohol, or derivative thereof, wherein said terpene is a monoterpene, sesquiterpene, diterpene, sesterterpene, or triterpene.

2.7 Compound 2, or any of 2.1-2.5, wherein A is the core of a terpene alcohol, or derivative thereof, wherein said terpene is a monoterpene or sesquiterpene.

2.8 Compound 2, or any of 2.1-2.5, wherein A is the core of a terpene alcohol, or derivative thereof, wherein said terpene is a monoterpene (e.g., A is an isodecyl moiety).

2.9 Compound 2, or any of 2.1-2.5, wherein A is the core of a terpene alcohol, or derivative thereof, wherein said terpene alcohol is selected from citronellol, isocitronellol, geraniol, nerol, menthol, myrcenol, linalool, thymol, α-terpineol, β-terpineol, Y-terpineol, borneol, farnesol, nerolidol, and carotol.

2.10 Compound 2.9, wherein said terpene alcohol is selected from citronellol, geraniol, nerol, myrcenol, linalool, and farnesol.

2.11 Compound 2.10, wherein said terpene alcohol is selected from citronellol, myrcenol, linalool, and farnesol.

2.12 Compound 2, or any of 2.1-2.5, wherein A is the core of a terpene alcohol, or derivative thereof, wherein said terpene alcohol, or derivative, is an oligomer of citronellol.

2.13 Compound 2 or any of 2.1-2.12, wherein said terpene alcohol, or derivative thereof, has its natural unsaturation.

2.14 Compound 2 or any of 2.1-2.12, wherein said terpene alcohol, or derivative thereof, is partially unsaturated (e.g., monounsaturated or diunsaturated).

2.15 Compound 2 or any of 2.2-2.12, wherein said terpene alcohol, or derivative thereof, is fully saturated (e.g., said terpene alcohol is a fully saturated monoterpene derivative, e.g., an isodecyl moiety).

2.16 Compound 2, or any of 2.1-2.5, wherein A is selected from the group consisting of:

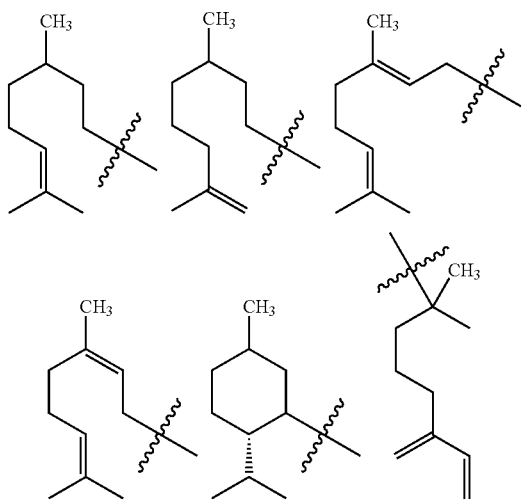

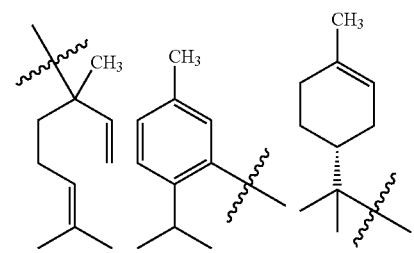
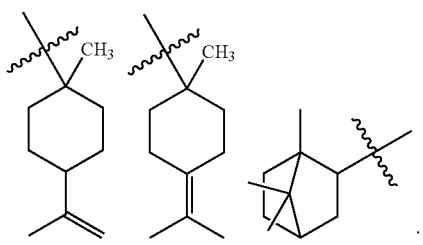
2.17 Compound 2, or any of 2.1-2.5, wherein A is selected from the group consisting of:
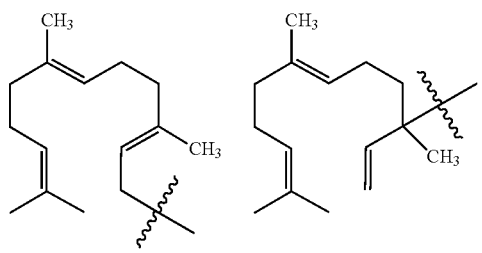
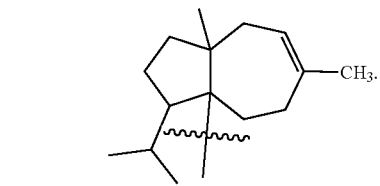
2.18 Compound 2, or any of 2.1-2.5, wherein A is selected from the group consisting of:
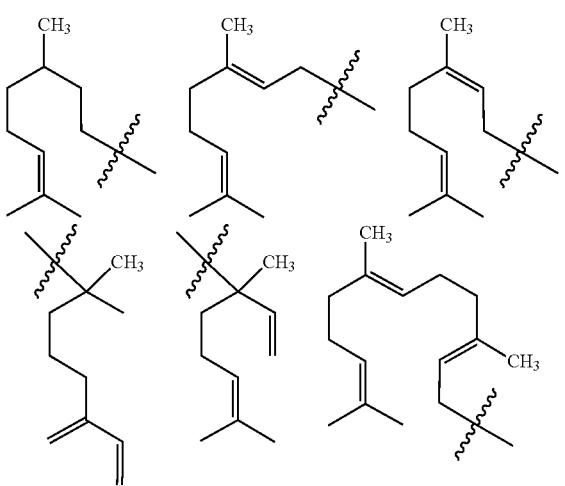
2.19 Compound 2, or any of 2.1-2.5, wherein A is selected from the group consisting of
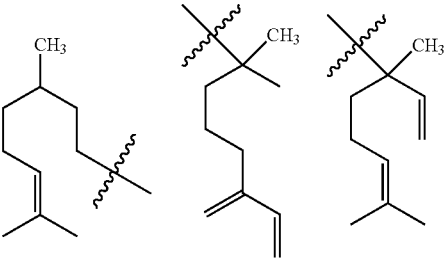
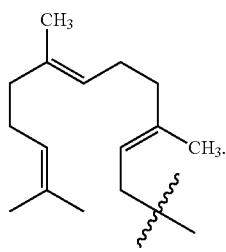
2.20 Compound 2, or any of 2.1-2.5, wherein A is:
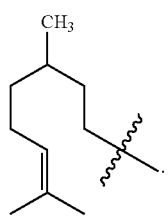 [SMILES: *CCC(C)CCC=C(C)C]
2.21 Compound 2, or any of 2.1-2.5, wherein A is selected from the group consisting of:
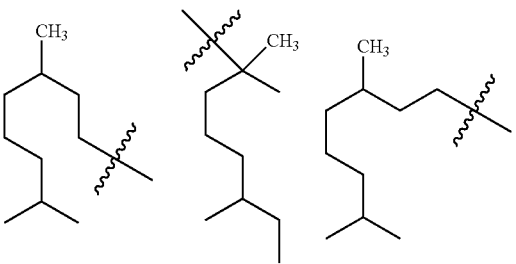

2.22 Compound 2, or any of 2.1-2.5, wherein A is selected from the group consisting of:
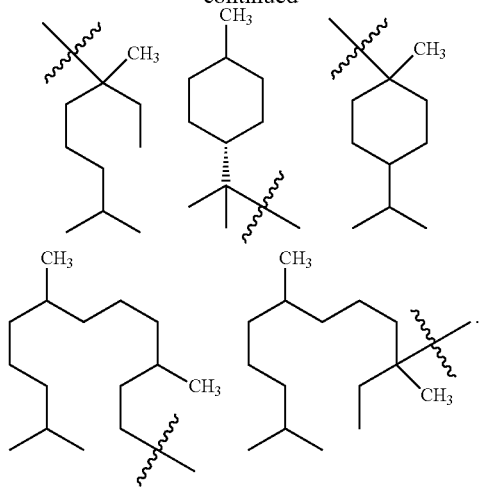
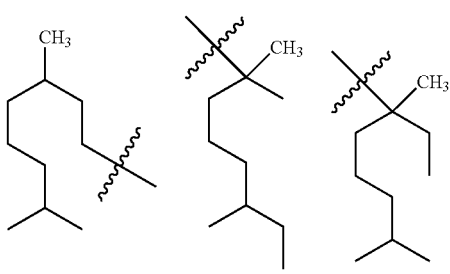
-continued
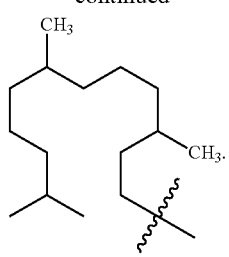
2.23 Compound 2, or any of 2.1-2.5, wherein A is:
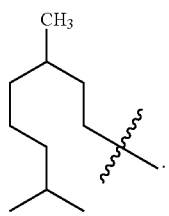 [SMILES: *CCC(C)CCCC(C)C]
2.24 Compound 2, or any of 2.1-2.5, wherein A is:
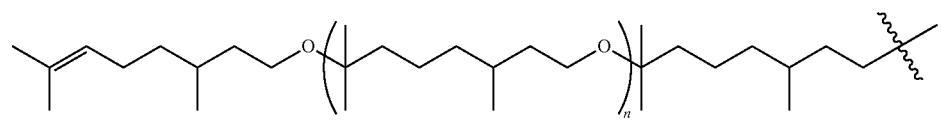
wherein n is an integer from 0-20 (e.g., 0-3, 0, 1 or 2).
2.25 Compound 2, or any of 2.1-2.5, wherein A is:
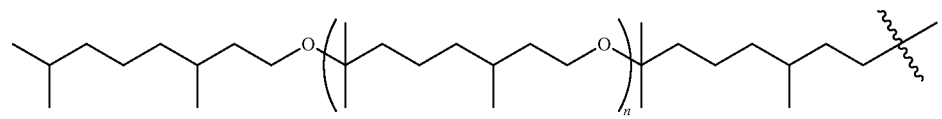

wherein n is an integer from 0-20 (e.g., 0-3, 0, 1 or 2).

2.26 Compound 2, or any of 2.1-2.25, wherein all substituents R are selected from H, C$_{1-6}$alkyl (e.g., methyl), and —(CO)—C$_{1-6}$alkyl (e.g., acetyl).

2.27 Compound 2.26, wherein all substituents R are H.

2.28 Compound 2.26, wherein at least half of the substituents R are H, and the other substituents R are C$_{1-6}$alkyl (e.g., methyl) or —(CO)—C$_{1-6}$alkyl (e.g., acetyl).

2.29 Compound 2, or any of 2.1-2.25, wherein one substituent R in the compound is a unit B, and all other substituents R are selected from H, C$_{1-6}$alkyl (e.g., methyl), and —(CO)—C$_{1-6}$alkyl (e.g., acetyl).

2.30 Compound 2.29, wherein the one substituent R which is a unit B is on the terminal glucose unit of the oligomer of Formula (II-P) or (III-P) (i.e., the glucose unit farthest from substituent A), optionally wherein each of said units B are the same unit B.

2.31 Compound 2, or any of 2.1-2.25, wherein one substituent R on each glucose unit is a unit B, and all other substituents R are selected from H, C$_{1-6}$alkyl (e.g., methyl), and —(CO)—C$_{1-6}$alkyl (e.g., acetyl).

2.32 Any one of compounds 2.29-2.31, wherein the substituent or substituents R which are a unit B, are the substituent or substituents R located on the 6-carbon hydroxy group of the glucose unit or units.

2.33 Any one of compounds 2.29-2.31, wherein the substituent or substituents R which are a unit B, are the substituent or substituents R located on the 4-carbon hydroxy group of the glucose unit or units.

2.34 Any one of compounds 2.29-2.31, wherein all other substituents R (which are not units B) are H.

2.35 Any one of compounds of 2.39-2.34, wherein the unit or units B are each the core of a terpene alcohol, or derivative thereof, wherein said terpene is a monoterpene, sesquiterpene, diterpene, sesterterpene, or triterpene.

2.36 Compound 2.35, wherein B is the core of a terpene alcohol, or derivative thereof, wherein said terpene is a monoterpene or sesquiterpene.

2.37 Compound 2.35, wherein B is the core of a terpene alcohol, or derivative thereof, wherein said terpene is a monoterpene (e.g., A is an isodecyl moiety).

2.38 Compound 2.35, wherein B is the core of a terpene alcohol, or derivative thereof, wherein said terpene alcohol is selected from citronellol, isocitronellol, geraniol, nerol, menthol, myrcenol, linalool, thymol, α-terpineol, β-terpineol, γ-terpineol, borneol, farnesol, nerolidol, and carotol.

2.39 Compound 2.38, wherein said terpene alcohol is selected from citronellol, geraniol, nerol, myrcenol, linalool, and farnesol.

2.40 Compound 2.39, wherein said terpene alcohol is selected from citronellol, myrcenol, linalool, and farnesol.

2.41 Compound 2.35, wherein B is the core of a terpene alcohol, or derivative thereof, wherein said terpene alcohol, or derivative, is an oligomer of citronellol.

2.42 Any one of compounds of 2.29-2.41, wherein said terpene alcohol, or derivative thereof, has its natural unsaturation.

2.43 Any one of compounds of 2.29-2.41, wherein said terpene alcohol, or derivative thereof, is partially unsaturated (e.g., monounsaturated or diunsaturated).

2.44 Any one of compounds of 2.29-2.41, wherein said terpene alcohol, or derivative thereof, is fully saturated (e.g., said terpene alcohol is a fully saturated monoterpene derivative, e.g., an isodecyl moiety).

2.45 Compound 2.35, wherein B is selected from the group consisting of:

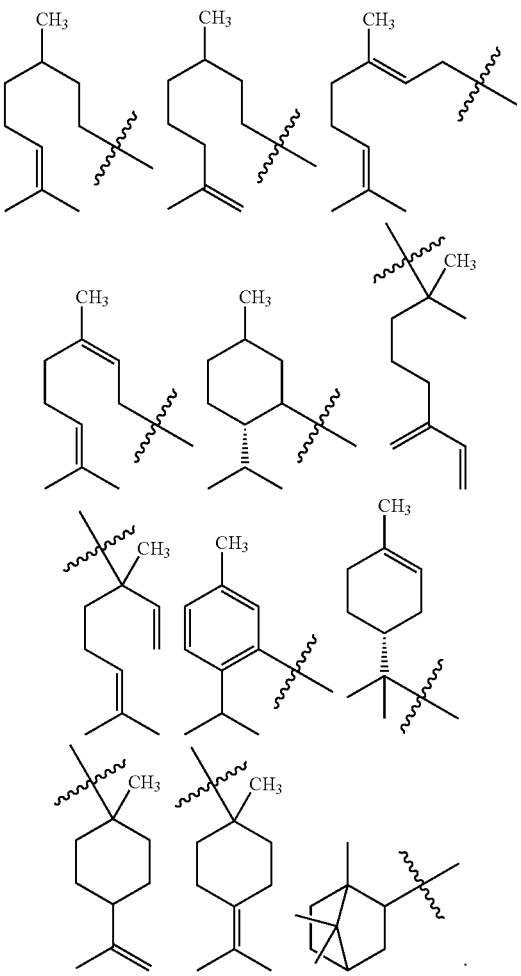

2.46 Compound 2.35, wherein B is selected from the group consisting of:

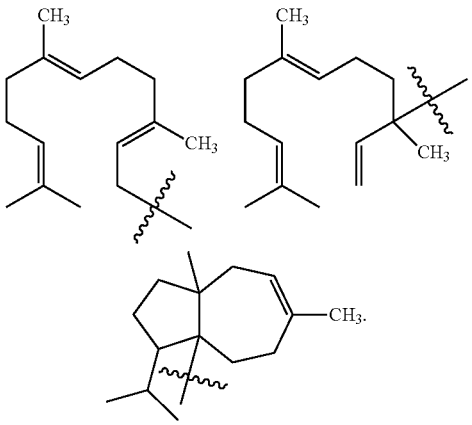

2.47 Compound 2.35, wherein B is selected from the group consisting of:
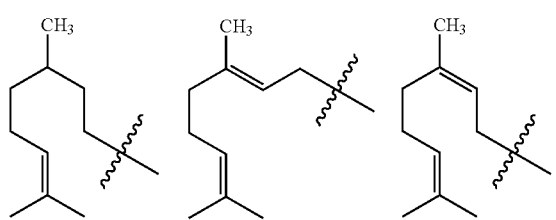
2.48 Compound 2.35, wherein B is selected from the group consisting of:
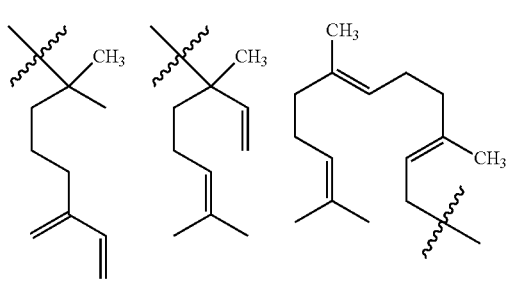
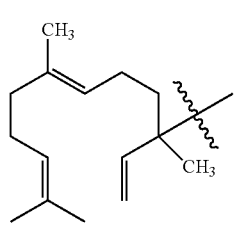
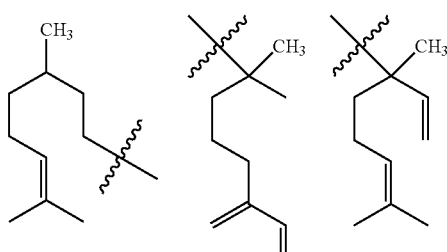
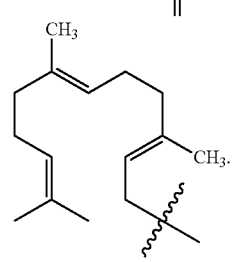
2.49 Compound 2.35, wherein B is:
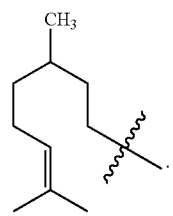 [SMILES: *CCC(C)CCC=C(C)C]
2.50 Compound 2.35, wherein B is selected from the group consisting of:
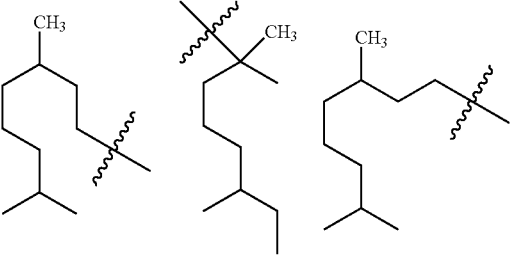
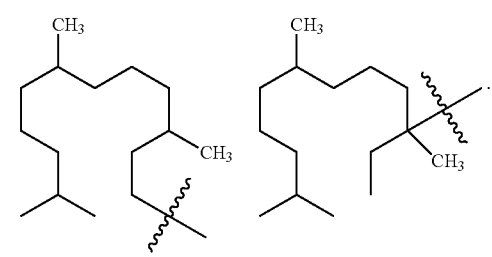
2.51 Compound 2.35, wherein B is selected from the group consisting of:
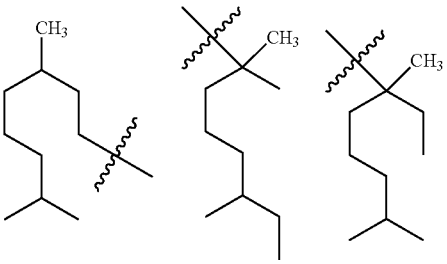

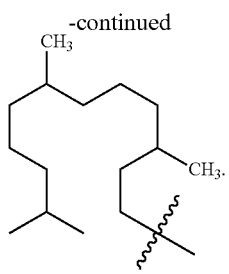

2.52 Compound 2.35, wherein B is:

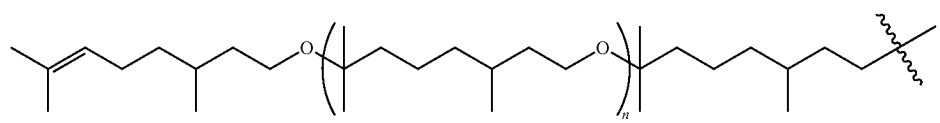

wherein n is an integer from 0-20 (e.g., 0-3, 0, 1 or 2).

2.53 Compound 2.35, wherein B is:

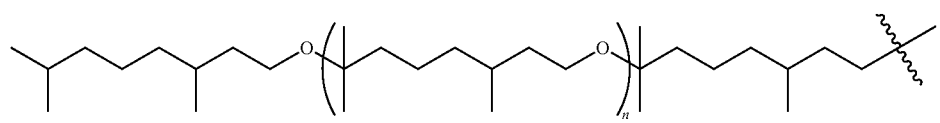

wherein n is an integer from 0-20 (e.g., 0-3, 0, 1 or 2).

2.54 Compound 2, or any of 2.1-2.53, wherein group A is an isodecyl group, e.g., selected from 2,4-dimethyloctan-2-yl, 2,6-dimethyl-octan-1-yl, 2,6-dimethyloctan-2-yl, 3,7-dimethyloctan-1-yl, and 3,7-dimethyloctan-3-yl.

2.55 Compound 2, or any of 2.1-2.54, wherein group B is an isodecyl group, e.g., selected from 2,4-dimethyloctan-2-yl, 2,6-dimethyl-octan-1-yl, 2,6-dimethyloctan-2-yl, 3,7-dimethyloctan-1-yl, and 3,7-dimethyloctan-3-yl.

2.56 Compound 2, or any of 2.1-2.55, wherein the compound is a compound of Formula II-P having the formula:

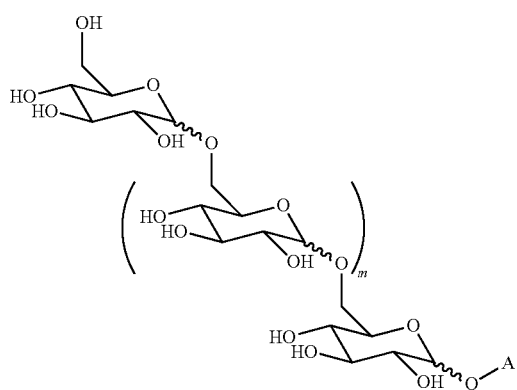

and wherein A is selected from the group consisting of:

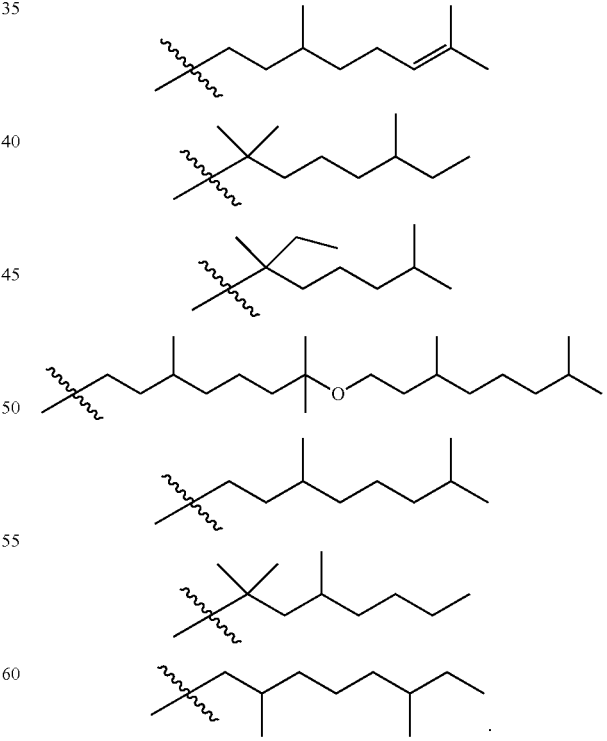

2.57 Compound 2, or any of 2.1-2.53, wherein the compound is a compound of Formula III-P having the formula:

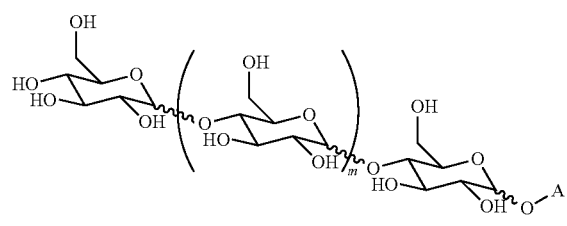
and wherein A is selected from the group consisting of:
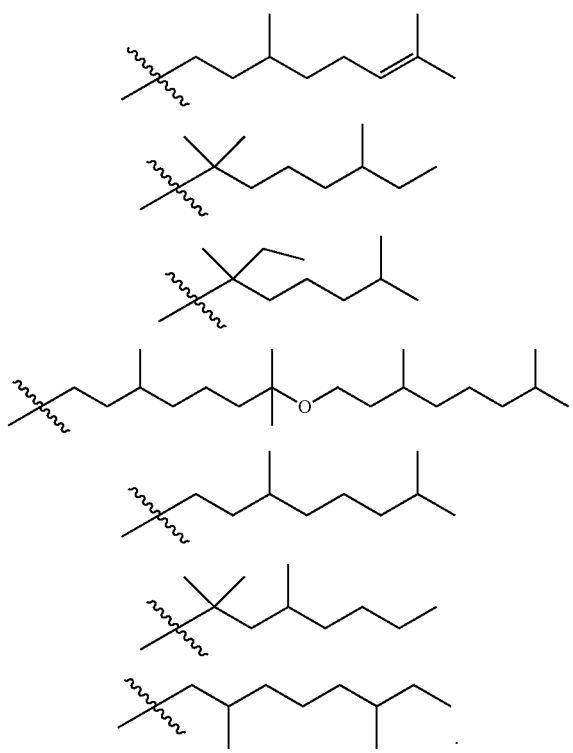
2.58 Compound 2, or any of 2.1-2.55, wherein the compound is a compound of Formula II-P having the formula:
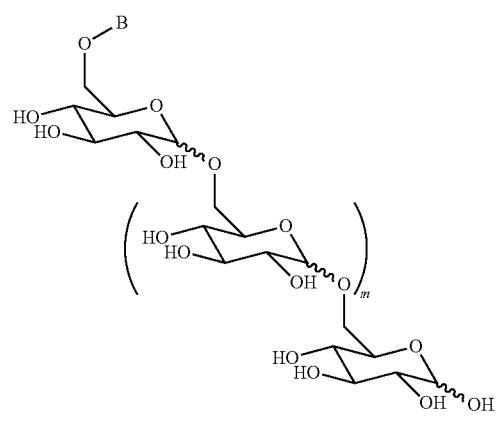
and wherein B is selected from the group consisting of:
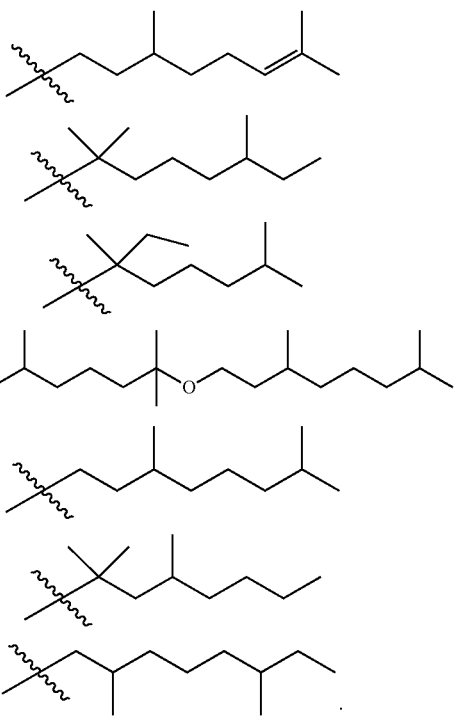
2.59 Compound 2, or any of 2.1-2.55, wherein the compound is a compound of Formula III-P having the formula:
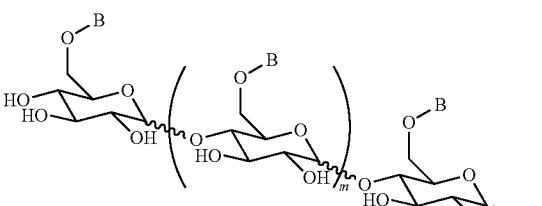
and wherein each B is H or is selected from the group consisting of:
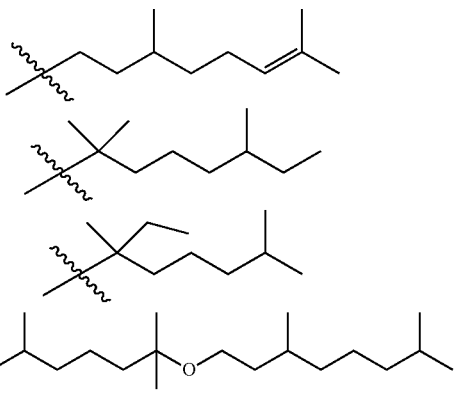

-continued

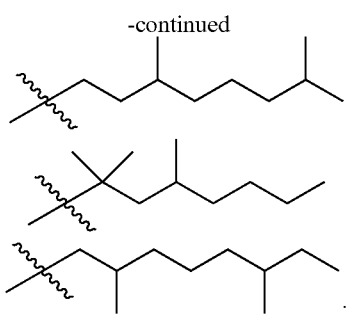

2.60 Any compounds 2.1-2.59, wherein the compound has a single stereogenic center within the substituent A, and each of any substituents B, and those centers have the R configuration.
2.61 Any compounds 2.1-2.59, wherein the compound has a single stereogenic center within the substituent A, and each of any substituents B, and those centers have the S configuration.
2.62 Any compounds 2.1-2.59, wherein the compound has two or three stereogenic centers within the substituent A, and each of any substituents B, and those centers all have the R configuration.
2.63 Any compounds 2.1-2.59, wherein the compound has two or three stereogenic centers within the substituent A, and each of any substituents B, and those centers all have the S configuration.
2.64 Compound 2, or any of 2.1-2.63, wherein one or more of the glucoside units of the compounds of Formula II-P or III-P is replaced by an alternative glycoside unit, for example, selected from another aldohexose (e.g., allose, altrose, mannose, gulose, idose, galactose or talose), wherein in all of the other features of the structure are as provided in Compound 2 or any of 2.1-2.63.
2.65 Compound 2, or any of 2.1-2.63, wherein one or more of the glucoside units of the compounds of Formula II-P or III-P is replaced by an alternative glycoside unit, for example, selected from a ketohexose (e.g., psicose, fructose, sorbose, tagatose), wherein in all of the other features of the structure are as provided in Compound 2 or any of 2.1-2.63, except that the ketohexose may be drawn as a furanose ring.
2.66 Compound 2, or any of 2.1-2.65, wherein the compound has a refractive index from 1.35 to 1.55, e.g., 1.40 to 1.50, or 1.42 to 1.48, or 1.43 to 1.46, or 1.44-1.45.
2.67 Compound 2, or any of 2.1-2.66, wherein the compound has a surface tension of 15 to 35 mN/m, e.g., 20 to 30 mN/m, or 22 to 28 mN/m, or 23 to 27 mN/m, or 24 to 26 mN/m, or about 25 mN/m.

The term "isodecyl" as used herein refers to any 10-carbon saturated alkyl chain that is not linear (i.e., not n-decyl).

The compounds provided by the present disclosure offer numerous improved benefits over existing compounds used for the same purpose. For example, Compound 1 et seq. and Compound 2 et seq. provide one or more of: (a) lower melting point, (b) better lubricity, (c) better spreading (e.g., better spontaneous spreading on the skin), (d) higher refractive index, (e) better hydrolytic stability, and (f) better enzymatic stability. Without being bound by theory, it is believed that compounds as disclosed herein having an isodecyl group are provide particularly beneficial improvements over compounds of the prior art, for example, due to the increased extent of branching in the alkyl chain. Surface tension is one of the physical factors which helps provide the compounds with improved emolliency, lubricity, spreadability and "play" (i.e., feel on the skin and hair) compared to known compounds used for similar purposes. Preferably, compounds of the present disclosure have a surface tension between 15 and 35 milliNewtons/meter (mN/m). Refractive index is important from an appearance standpoint, as a higher refractive index provides for a shinier or glossier product. Preferably, compounds of the present disclosure have a refractive index between 1.35 and 1.55.

The term "alkyl" as used herein refers to a monovalent or bivalent, branched or unbranched saturated hydrocarbon group having from 1 to 20 carbon atoms, typically although, not necessarily, containing 1 to about 12 carbon atoms, such as methyl, ethyl, n-propyl, isopropyl, n-butyl, isobutyl, t-butyl, octyl, and the like. The term alkyl also may include cycloalkyl groups. Thus, for example, the term C6 alkyl would embrace cyclohexyl groups, the term C5 would embrace cyclopentyl groups, the term C4 would embrace cyclobutyl groups, and the term C3 would embrace cyclopropyl groups. In addition, as the alkyl group may be branched or unbranched, any alkyl group of n carbon atoms would embrace a cycloalkyl group of less than n carbons substituted by additional alkyl substituents. Thus, for example, the term C6 alkyl would also embrace methylcyclopentyl groups, or dimethylcyclobutyl or ethylcyclobutyl groups, or trimethylcyclopropyl, ethylmethylcyclopropyl or propylcyclopropyl groups.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like. In like manner as for the term "alkyl", the term "alkenyl" also embraces cycloalkenyl groups, both branched an unbranched with the double bond optionally intracyclic or exocyclic.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like. In like manner as for the term "alkyl", the term "alkynyl" also embraces cycloalkynyl groups, both branched an unbranched, with the triple bond optionally intracyclic or exocyclic.

The term "aryl" as used herein refers to an aromatic hydrocarbon moiety comprising at least one aromatic ring of 5-6 carbon atoms, including, for example, an aromatic hydrocarbon having two fused rings and 10 carbon atoms (i.e., a naphthalene).

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

The terms "branched" and "linear" (or "unbranched") when used in reference to, for example, an alkyl moiety of $C_a$ to $C_b$ carbon atoms, applies to those carbon atoms defining the alkyl moiety. For example, for a $C_4$ alkyl moiety, a branched embodiment thereof would include an isobutyl, whereas an unbranched embodiment thereof would be an n-butyl. However, an isobutyl would also qualify as a linear $C_3$ alkyl moiety (a propyl) itself substituted by a $C_1$ alkyl (a methyl).

Unless otherwise specified, any carbon atom with an open valence may be substituted by an additional functional group. Examples of functional groups include, without limitation: halo, hydroxyl, sulfhydryl, $C_1$-$C_{20}$ alkoxy, $C_2$-$C_{20}$ alkenyloxy, $C_2$-$C_{20}$ alkynyloxy, $C_5$-$C_{20}$ aryloxy, acyl (including $C_2$-$C_{20}$ alkylcarbonyl (—CO-alkyl) and $C_6$-$C_{20}$ arylcarbonyl (—CO-aryl)), acyloxy (—O-acyl), $C_2$-$C_{20}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{20}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH_2), mono-substituted $C_1$-$C_{20}$ alkylcarbamoyl (—(CO)—NH($C_1$-C20 alkyl)), di-substituted alkylcarbamoyl (—(CO)—N($C_1$-C20 alkyl)_2), mono-substituted arylcarbamoyl (—(CO)—NH-aryl), thiocarbamoyl (—(CS)—NH_2), carbamido (—NH—(CO)—NH_2), cyano (—C≡N), isocyano (—N⁺≡C⁻), cyanato (—O—C≡N), isocyanato (—O—N⁺≡C⁻), isothiocyanato (—S—C≡N), azido (—N=N⁺=N⁻), formyl (—(CO)—H), thioformyl (—(CS)—H), amino (—NH_2), mono- and di-($C_1$-$C_{20}$ alkyl)-substituted amino, mono- and di-($C_5$-$C_{20}$ aryl)-substituted amino, $C_2$-$C_{20}$ alkylamido (—NH—(CO)-alkyl), $C_5$-$C_{20}$ arylamido (—NH—(CO)-aryl), imino (—CR=NH where R=hydrogen, $C_1$-C20 alkyl, $C_5$-$C_{20}$ aryl, $C_6$-$C_{20}$ alkaryl, $C_6$-$C_{20}$ aralkyl, etc.), alkylimino (—CR=N (alkyl), where R=hydrogen, alkyl, aryl, alkaryl, etc.), arylimino (—CR=N (aryl), where R=hydrogen, alkyl, aryl, alkaryl, etc.), nitro (—NO_2), nitroso (—NO), sulfo (—SO_2—OH), sulfonato (—SO_2—O⁻), $C_1$-$C_{20}$ alkylsulfanyl (—S-alkyl; also termed "alkylthio"), arylsulfanyl (—S-aryl; also termed "arylthio"), $C_1$-$C_{20}$ alkylsulfinyl (—(SO)-alkyl), $C_5$-$C_{20}$ arylsulfinyl (—(SO)-aryl), $C_1$-$C_{20}$ alkylsulfonyl (—SO_2-alkyl), $C_5$-$C_{20}$ arylsulfonyl (—SO_2-aryl), phosphono (—P(O)(OH)_2), phosphonato (—P(O)(O⁻)_2), phosphinato (—P(O)(O⁻)), phospho (—PO_2), -phosphino (—PH_2), mono- and di-($C_1$-$C_{20}$ alkyl)-substituted phosphino, mono- and di-($C_5$-$C_{20}$ aryl)-substituted phosphino; and the hydrocarbyl moieties such as $C_1$-C20 alkyl (including $C_1$-$C_{18}$ alkyl, further including $C_1$-$C_{12}$ alkyl, and further including $C_1$-$C_6$ alkyl), $C_2$-$C_{20}$ alkenyl (including $C_2$-$C_{18}$ alkenyl, further including $C_2$-$C_{12}$ alkenyl, and further including $C_2$-$C_6$ alkenyl), $C_2$-$C_{20}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{20}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

In a second aspect, the present disclosure provides a method (Method 1) of making the Compound 1, et seq., comprising the step of reacting a compound of the Formula A, with a glucose or glucoside compound of Formula B corresponding to the glycone portion of the Compound 1, in a condensation reaction to form the compound of Formula I, II, II-P, III, or III-P:

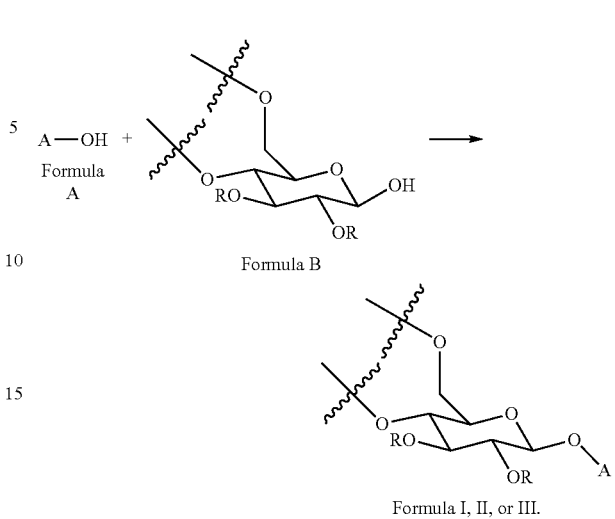

Formula A
Formula B
Formula I, II, or III.

Wherein substituents A and R, are as defined hereinabove. In some embodiments, the reaction is conducted by reacting the compound of Formula A and the compound of Formula B in the presence of an acid catalyst, optionally under dehydrating conditions. Preferably, the acid catalyst is selected from sulfuric acid, hydrochloric acid, phosphoric acid, toluenesulfonic acid, methanesulfonic acid, or an acidic ion exchange resin, such as an Amberlyst-type resin. In some embodiments, the reaction further comprises a dehydrating agent, such as sodium sulfate, magnesium sulfate, phosphorus pentoxide, or the like. In a preferred embodiment, the reaction comprises a mixture of sulfuric acid and magnesium sulfate, optionally in a hydrocarbon solvent, such as heptane, or a hydrocarbon solvent and a more polar co-solvent. In some embodiments, the magnesium sulfate is first suspended in a hydrocarbon solvent, such as heptane, and concentration sulfuric acid is added to form, after removal of the solvent, a solid $MgSO_4/H_2SO_4$ adduct which can be used directly as an acidic catalyst for the condensation reaction. Preferably, this solid adduct is added directly to the neat reaction components (e.g., where the terpene alcohol of Formula A and/or the acid of Formula B is a liquid). In some embodiments, the reaction is conducted by reacting the compound of Formula A with an activated derivative of the compound of Formula B, such as a halide or sulfonate of the compound of Formula B. In some embodiments, the reaction is conducted by reacting the compound of Formula B with an activated derivative of the compound of Formula A, such as a halide or sulfonate of the compound of Formula A.

In some embodiments, the above reaction is carried on a compound of Formula B wherein all R groups are H, to form a compound of Formula I, II, II-P, III, or III-P, wherein all R groups are H. Optionally, in a subsequent step, the resulting compound of Formula I, II, II-P, III, or III-P, wherein all R groups are H may be further reacted with a suitable reagent, e.g., an alkyl halide or an acyl halide or acid anhydride, under suitable conditions, to form a compound of Formula I, II, II-P, III, or III-P, wherein one or more groups R are $C_{1-6}$alkyl or CO—$C_{1-6}$alkyl. In other embodiments, the above reaction (with A-OH) is carried out on a compound of Formula B which already comprises R groups other than H.

In another embodiment of the second aspect, the present disclosure provides a method of making the Compound 1, et seq., comprising the step of reacting a compound of the Formula E, with a compound of Formula B in an electrophilic alkene addition reaction to form the compound of Formula I, II, II-P, III, or III-P, provided that the compound of Formula E is formable by the dehydration of a compound of Formula A:

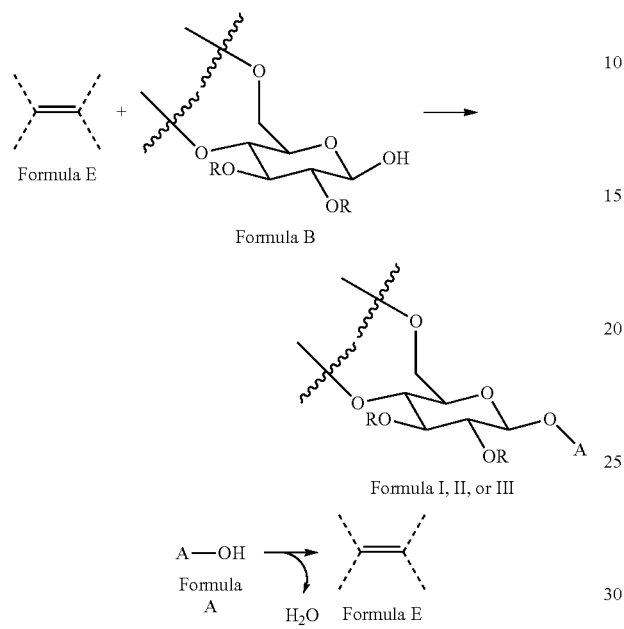

Wherein substituents A and B, are as defined hereinabove, and wherein the structure of Formula E is contingent on the structure of Formula A, such that elimination of the OH group and an H atom from adjacent carbon atoms will result in the compound of Formula E. Such an addition reaction may proceed under acidic conditions, by combining the compound of Formula E and the compound of Formula B in the presence of an acid catalyst, using conditions, for example, as described in the preceding paragraph. The dehydration reaction may also proceed under acidic conditions, by combining the compound of Formula A with an acid catalyst, optionally under dehydrating conditions, for example, using conditions described in the preceding paragraph.

For example, a compound of Formula A having each of the following partial structures may provide, by elimination of water, the corresponding compound of Formula E:

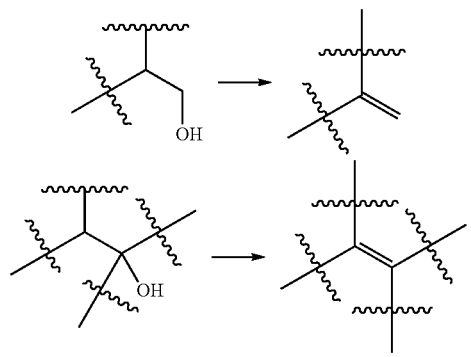

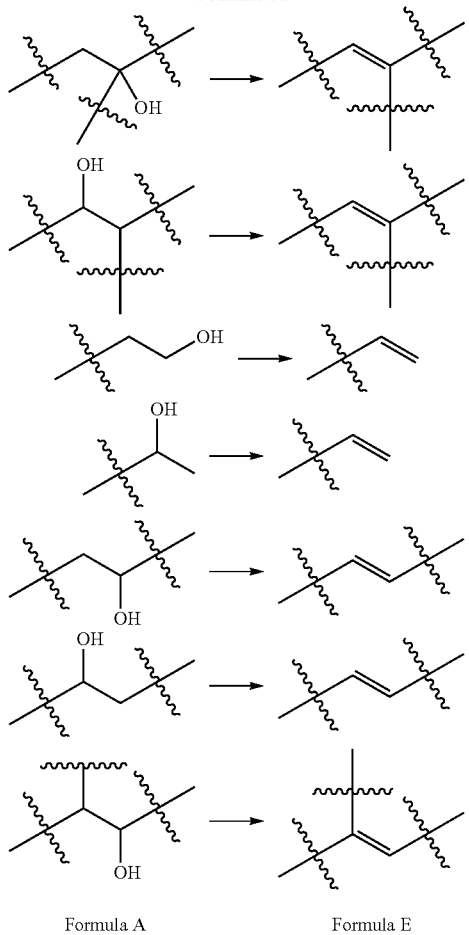

Formula A      Formula E

Suitable solvents and reactions conditions (concentration, time, temperature) for the conducting the reactions are generally known to those skilled in the art and are not limited in any way in the present disclosure. Depending on the choice of reagents, suitable solvents may include one or more of apolar, polar protic and/or polar aprotic solvents, for example hydrocarbons, ethers, and esters. In particular, for the reactions of the present disclosure, owing to the high hydrophilicity of the carbohydrate starting materials and the high hydrophobicity of the terpene starting materials, it may be necessary to employ solvent mixtures comprising a hydrophobic solvent (e.g., hydrocarbons, aromatics, chlorinated hydrocarbons) in combination with one more hydrophilic co-solvents (e.g., alcohols, ethers, esters). In some embodiments, the reaction may further comprise a phase-transfer reagent or surfactants.

In some embodiments, the reaction is carried out at a temperature of −25° C. to 200° C. In a preferred embodiment, the reaction is run at 25 to 150° C., or 50 to 100° C. In some embodiments, the reaction is carried out for 0.1 to 100 hours. In a preferred embodiment the reaction is run for 0.5-12 hours, or 0.5 to 6 hours, or 1 to 3 hours.

In another embodiment of the second aspect, the present disclosure provides a method (Method 2) of making the Compound 2, et seq., comprising the step of reacting a compound of the Formula A, with a glycoside polymer of Formula B (e.g., a cellulose) corresponding to the glycone portion of the Compound 2, in a condensation reaction to form the compound of Formula II, III, II-P. or III-P, according to any of the embodiments of Method 1 above.

The compound Formula A, and the compound of Formula B (if applicable) used to make the Compound 1 et seq. of the present disclosure, is (are) a terpene alcohol or a derivative thereof (e.g., a hydrogenated terpene alcohol). Preferably the terpene alcohol is obtained from or isolated from a natural renewable resource. For example, the each of the following terpene alcohols can be obtained by extraction from numerous plant species: citronellol, isocitronellol, geraniol, nerol, menthol, myrcenol, linalool, thymol, α-terpincol, β-terpineol, γ-terpincol, borneol, farnesol, nerolidol, and carotol. The essential oils of many trees and plants, such as rose oil, palmarosa oil, citronella oil, lavender oil, coriander oil, thyme oil, peppermint oil, and pine oil, have significant amounts of these terpene alcohols.

In a preferred embodiment, however, the terpene alcohols may be derived semi-synthetically (e.g., by double bond hydration reactions) from naturally derived terpenes. Terpenes are much more abundant in nature than the corresponding terpene alcohols. Common terpenes include: alpha-pinene, beta-pinene, alpha-terpinene, beta-terpinene, gamma-terpinene, delta-terpinene (terpinolene), myrcene, limonene, camphene, carene, sabinene, alpha-ocimene, beta-ocimene, alpha-thujene, and beta-thujene. Alpha-pinene is the most abundant naturally occurring terpene in nature, being present in a high concentration in various tree resins and oils, such as pine oil and oleoresin (and its derivative turpentine). Numerous terpene oils can be derived from the terpenes present in turpentine, pine oil, and similar materials. Turpentine is a major by-product of the paper and pulp industries, so using this material as a source for terpene alcohols would be both economical and environmentally friendly.

In addition, the terpene alcohols can be prepared semi-synthetically from either isobutylene, isoprenol, or ethanol. Ethanol, as well as methanol and tert-butanol, can be derived in large volumes from the fermentation of biorenewable sugars, such as from corn, cane sugar or beet sugar. Isobutylene can be derived from tert-butanol by elimination or from ethanol by mixed oxidation to acetaldehyde and acetone and aldol condensation, and isoprenol can be derived from isobutylene by reaction with formaldehyde, and formaldehyde can be made by oxidation of methanol. Methanol and ethanol can also be derived from the by-product fractions from commercial ethanol distillation (e.g., in the making of spirits). By these routes, the Compounds of the present disclosure can all be made entirely from biorenewable resources such as trees and plants.

Thus, in some embodiments of the present disclosure, the Method of making Compound 1 et seq. may further comprise one or more of the following steps: (1) harvesting of one or more crops or grains (e.g., corn, beets, sugarcane, barley, wheat, rye, or sorghum), (2) fermenting such harvested crops or grains, (3) obtaining from such fermentation one or more $C_{1-4}$ aliphatic alcohols (e.g., methanol, ethanol, isobutanol, tert-butanol, or any combination thereof), (4) converting said alcohols to isobutylene and/or isoprenol. (5) converting said isobutylene or isoprenol to one or more terpenes (e.g., alpha-pinene, beta-pinene, alpha-terpinene, beta-terpinene, gamma-terpinene, delta-terpinene (terpinolene), myrcene, limonene, camphene, carene, sabinene, alpha-ocimene, beta-ocimene, alpha-thujene, and beta-thujene); (6) extracting or isolating one or more terpenes from naturally occurring plant and tree extracts, such as essential oils and resins (e.g., rosin, dammars, mastic, sandarac, frankincense, elemi, turpentine, copaiba, oleoresin, pine oil, cannabis oil, coriander oil), and (7) converting such terpenes to one or more terpene alcohols (e.g., citronellol, isocitronellol, geraniol, nerol, menthol, myrcenol, linalool, thymol, α-terpineol, β-terpineol, γ-terpineol, borneol, farnesol, nerolidol, and carotol).

In another aspect, the present disclosure provides a composition comprising Compound 1 or any of 1.1 to 1.69, or any of Compound 2 or any of 2.1 to 2.67, optionally in admixture with one or more pharmaceutically acceptable, cosmetically acceptable, or industrially acceptable excipients or carriers, for example, solvents, oils, surfactants, emollients, diluents, glidants, abrasives, humectants, polymers, plasticizer, catalyst, antioxidant, coloring agent, flavoring agent, fragrance agent, antiperspirant agent, antibacterial agent, antifungal agent, hydrocarbon, stabilizer, or viscosity controlling agent. In some embodiments, the composition is a pharmaceutical composition, or a cosmetic composition, or a sunscreen composition, or a plastic composition, or a lubricant composition, or a personal care composition (e.g., a soap, skin cream or lotion, balm, shampoo, body wash, hydrating cream, deodorant, antiperspirant, aftershave lotion, cologne, perfume, or other hair care or skin care product), or a cleaning composition (e.g., a surface cleaner, a metal cleaner, a wood cleaner, a glass cleaner, a body cleaner such as a soap, a dish-washing detergent, or a laundry detergent), or an air freshener.

In preferred embodiments, such Compositions comprise a Compound according to the present disclosure having an isodecyl group. In a particularly preferred embodiment, such Compositions also comprise another excipient having a decyl or isodecyl group, such as, decyl or isodecyl alcohol, decanoic or isodecanoic acids, decyl or isodecyl ethers, or decyl or isodecyl esters. For example, such Compositions may comprise a combination of one or more of the isodecyl compounds of Examples 1 to 5.

The compounds of the present disclosure, e.g., Compound 1, et seq., or Compound 2 et seq., may be used with, e.g.: perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, anti-perspirants, shampoo, cologne, shower gel, hair spray, and pet litter.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

In some embodiments, the present disclosure provides personal care compositions including, but not limited to, soaps (liquid or solid), body washes, skin and hair cleansers, skin creams and lotions (e.g., facial creams and lotions, face oils, eye cream, other anti-wrinkle products), ointments, sunscreens, moisturizers, hair shampoos and/or conditioners, deodorants, antiperspirants, other conditioning products for the hair, skin, and nails (e.g., shampoos, conditioners, hair sprays, hair styling gel, hair mousse), decorative cosmetics (e.g., nail polish, eye liner, mascara, lipstick, foundation, concealer, blush, bronzer, eye shadow, lip liner, lip balm,) and dermocosmetics.

In some embodiments, the personal care compositions may include organically-sourced ingredients, vegan ingredients, gluten-free ingredients, environmentally-friendly ingredients, natural ingredients (e.g. soy oil, beeswax, rosemary oil, vitamin E, coconut oil, herbal oils etc.), comedogenic ingredients, natural occlusive plant based ingredients (e.g. cocoa, shea, mango butter), non-comedogenic ingredients, bakuchiol (a plant derived compound used as a less-irritating, natural alternative to retinol), color active ingredients (e.g., pigments and dyes); therapeutically-active ingredients (e.g., vitamins, alpha hydroxy acids, corticosteroids, amino acids, collagen, retinoids, antimicrobial compounds), sunscreen ingredients and/or UV absorbing compounds, reflective compounds, oils (such as castor oil and olive oil, or high-viscosity oils), film formers, high molecular weight esters, antiperspirant active ingredients, glycol solutions, water, alcohols, emulsifiers, gellants, emollients, water, polymers, hydrocarbons, conditioning agents, and/or aliphatic esters.

In some embodiments, the present compositions are gluten free.

In some embodiments, the present compositions are formulated as oil-in-water emulsions, or as water-in-oil emulsions. In some embodiments, the compositions may further comprise one or more hydrocarbons, such as heptane, octane, nonane, decane, undecane, dodecane, isododecane, tridecane, tetradecane, pentadecane, hexadecane, heptadecane, octadecane, nonadecane, henicosane, docosane, and tricosane, and any saturated linear or saturated branched isomer thereof.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore, as used herein, the terms "may," "optional," "optionally." or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

In the present specification, the structural formula of the compounds represents a certain isomer for convenience in some cases, but the present invention includes ail isomers, such as geometrical isomers, optical isomers based on an asymmetrical carbon, stereoisomers, tautomers, and the like. In addition, a crystal polymorphism may be present for the compounds represented by the formulas describe herein. It is noted that any crystal form, crystal form mixture, or anhydride or hydrate thereof is included in the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as Na+, K+, Li+, alkali earth metal salts such as Mg2+ or Ca2+, or organic amine salts, or organic phosphonium salts.

All percentages used herein, unless otherwise indicated, are by volume.

All ratios used herein, unless otherwise indicated, are by molarity.

Although specific embodiments of the present disclosure have been described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

EXAMPLES

Having been generally described herein, the follow non-limiting examples are provided to further illustrate this invention.

The compounds disclosed herein can be prepared through a number of straightforward etherification or transetherification processes. One preferred method involves the use of combinations of $MgSO_4$ and $H_2SO_4$, in a similar vein to that used for transesterification according to Wright, et al. in *Tetrahedron Letters*, Vol. 38, No. 42, pp. 7345-7348, 1997. In an even more preferred method, however, the $MgSO_4/H_2SO_4$ catalyst is prepared in advance from a non-polar organic solvent such as heptane.

In this approach the $MgSO_4$ is suspended in solution with stirring under inert atmosphere, (e.g., 10 g of $MgSO_4$ in 40 g of heptane), and concentrated $H_2SO_4$ is added dropwise to the solution. The mixture is stirred for some time, e.g., 15 minutes or 1 hour, and the heptane phase is then filtered off, leaving a white solid powder that can be further dried under vacuum or blown dry with inert air, e.g., nitrogen or argon. This white solid can then be used as a powerful esterification catalyst that is especially preferred for making tertiary esters from tertiary alcohols and/or suitably substituted olefins.

Example 1. Isodecyl Glucoside (1-O-α-(2,6-Dimethyloctan-1-yl)-4-O-α-glucopyranosyl-glucopyranoside)

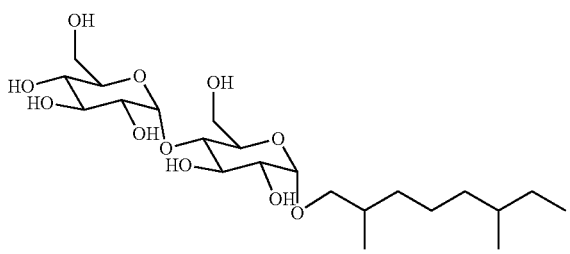 [SMILES: CCC(C)CCCC(C)COC1OC(CO)C(OC2OC(CO)C(O)C(O)C2O)C(O)C1O]

2,6-Dimethyloctanol (1 equivalent) is combined with maltose (1 equivalent) in hexane or heptane solvent, and 50 grams of the MgSO$_4$/H$_2$SO$_4$ solid catalyst per kilogram of 2,6-dimethyloctanol is added under an inert atmosphere in a 5-liter glass reactor vessel. The solution is then stirred for 8 hours at 80° C. with nitrogen bubbling. The gas outlet of the glass reactor is attached to a condenser to condense and collect excess methanol. The reaction is then brought to room temperature, and then 100 grams of potassium carbonate is slowly added to the solution. It is then stirred for 2 hours and filtered. Excess 2,6-dimethyloctanol and solvent are removed under reduced pressure and the desired product is further isolated by distillation.

Example 2. Isodecyl Glucoside (1-O-α-(2,4-dimethyloctan-2-yl)-4-O-α-glucopyranosyl-glucopyranoside)

2,4-Dimethyloctan-2-ol (1 equivalent) is combined with maltose (1 equivalent) in hexane or heptane solvent, and 50 grams of the MgSO$_4$/H$_2$SO$_4$ solid catalyst per kilogram of 2,4-dimethyloctan-2-ol is added under an inert atmosphere in a 5-liter glass reactor vessel. The solution is then stirred for 8 hours at 80° C. with nitrogen bubbling. The gas outlet of the glass reactor is attached to a condenser to condense and collect excess methanol. The reaction is then brought to room temperature, and then 100 grams of potassium carbonate is slowly added to the solution. It is then stirred for 2 hours and filtered. Excess 2,4-dimethyloctan-2-ol and solvent are removed under reduced pressure and the desired product is further isolated by distillation.

Example 3. Isodecyl Glucoside (1-O-α-(3,7-dimethyloctan-1-yl)-4-O-α-glucopyranosyl-glucopyranoside)

3,7-Dimethyl-1-octanol (a.k.a. dihydrocitronellol or tetrahydrogeraniol) (1 equivalent) is combined with maltose (1 equivalent) in hexane or heptane solvent, and 50 grams of the MgSO$_4$/H$_2$SO$_4$ solid catalyst per kilogram of 3,7-dimethyl-1-octanol is added under an inert atmosphere in a 5-liter glass reactor vessel. The solution is then stirred for 8 hours at 80° C. with nitrogen bubbling. The gas outlet of the glass reactor is attached to a condenser to condense and collect excess methanol. The reaction is then brought to room temperature, and then 100 grams of potassium carbonate is slowly added to the solution. It is then stirred for 2 hours and filtered. Excess 3,7-dimethyl-1-octanol and solvent are removed under reduced pressure and the desired product is further isolated by distillation.

Example 4. Isodecyl Glucoside (1-O-α-(3,7-dimethyloctan-3-yl)-4-O-α-glucopyranosyl-glucopyranoside)

3,7-Dimethyl-3-octanol (a.k.a. tetrahydrolinalool) (1 equivalent) is combined with maltose (1 equivalent) in hexane or heptane solvent, and 50 grams of the MgSO$_4$/H$_2$SO$_4$ solid catalyst per kilogram of 3,7-dimethyl-3-octanol is added under an inert atmosphere in a 5-liter glass reactor vessel. The solution is then stirred for 8 hours at 80° C. with nitrogen bubbling. The gas outlet of the glass reactor is attached to a condenser to condense and collect excess methanol. The reaction is then brought to room temperature, and then 100 grams of potassium carbonate is slowly added to the solution. It is then stirred for 2 hours and filtered. Excess 3,7-dimethyl-3-octanol and solvent are removed under reduced pressure and the desired product is further isolated by distillation.

Example 5. Isodecyl Glucoside (1-O-α-(2,6-dimethyloctan-2-yl)-4-O-α-glucopyranosyl-glucopyranoside)

2,6-Dimethyloctan-2-ol (tetrahydromyrcenol) (1 equivalent) is combined with maltose (1 equivalent) in hexane or heptane solvent, and 50 grams of the MgSO$_4$/H$_2$SO$_4$ solid catalyst per kilogram of 2,6-dimethyloctan-2-ol is added under an inert atmosphere in a 5-liter glass reactor vessel. The solution is then stirred for 8 hours at 80° C. with nitrogen bubbling. The gas outlet of the glass reactor is attached to a condenser to condense and collect excess methanol. The reaction is then brought to room temperature, and then 100 grams of potassium carbonate is slowly added to the solution. It is then stirred for 2 hours and filtered. Excess 2,6-dimethyloctan-2-ol and solvent are removed under reduced pressure and the desired product is further isolated by distillation.

The compounds of the above Examples are believed to offer numerous improved benefits over existing compounds used for the same purpose. For example, these compounds may provide one or more of: (a) lower melting point, (b) better lubricity, (c) better spreading (e.g., better spontaneous spreading on the skin), (d) higher refractive index, (e) better hydrolytic stability, and (f) better enzymatic stability.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

I claim:

1. A terpene alcohol O-glycoside ether compound of the general formula (I):

Formula (I)

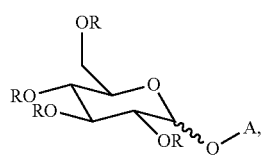

in free or salt form; or
a terpene alcohol (1→6)-O-glycoside ether compound of the general formula (II):

Formula (II)

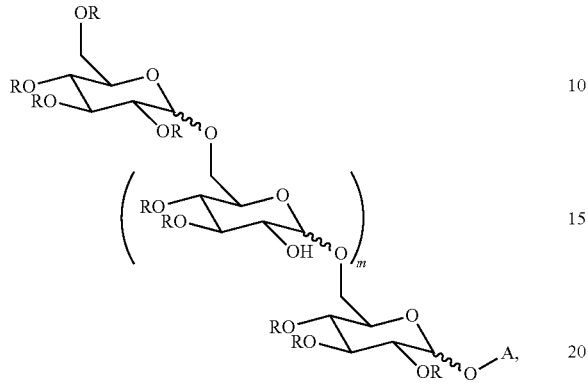

in free or salt form, wherein m is an integer from 0-10; or
a terpene alcohol (1→4)-O-glycoside ether compound of the general formula (III):

Formula (III)

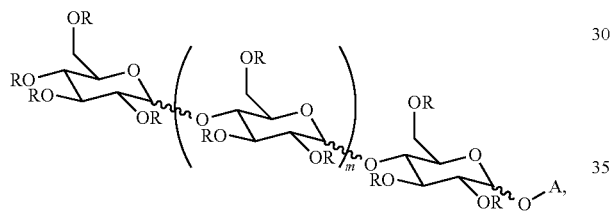

in free or salt form, wherein m is an integer from 0-10;
wherein in each of Formula (I) and Formula (II) and Formula (III):
A is selected from the group consisting of:

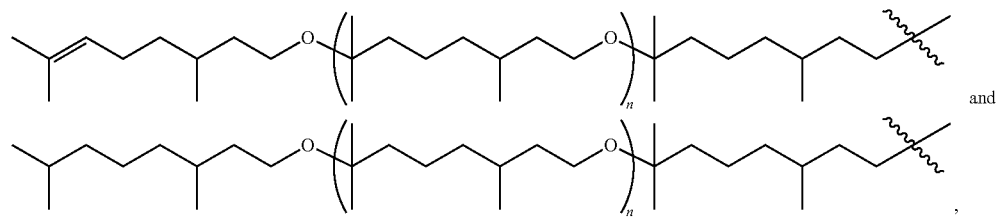

wherein n is an integer from 0-20;
and
each R is independently selected from H, $C_{1-6}$alkyl, and —(CO)—$C_{1-6}$alkyl.

2. The compound of claim 1, wherein the compound is the terpene O-glycoside ether compound of the general formula (I).

3. The compound of claim 1, wherein the compound is the terpene alcohol (1→6)-O-glycoside ether compound of the general formula (II).

4. The compound of claim 3, wherein m is 0.

5. The compound of claim 3, wherein m is selected from 1, 2, 3, 4, 5, or 6.

6. The compound of claim 1, wherein the compound is the terpene alcohol (1→4)-O-glycoside ether compound of the general formula (III).

7. The compound of claim 1, wherein all substituents R are selected from the group consisting of H, methyl and acetyl.

8. The compound of claim 1, wherein all substituents R are selected from $C_{1-6}$alkyl, and —(CO)—$C_{1-6}$alkyl.

9. The compound of claim 1, wherein all substituents R are H.

10. The compound of claim 1, wherein A is:

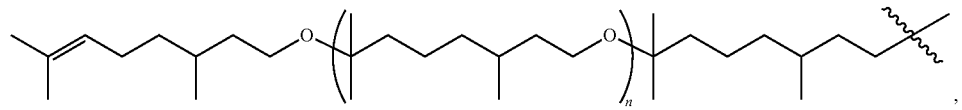
, wherein n is an integer from 0-20.

11. The compound of claim 10, wherein n is an integer selected from 0-3.

12. The compound of claim 10, wherein n is 0, 1, or 2.

13. The compound of claim 1, wherein A is:

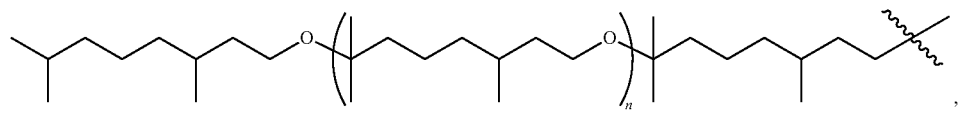
, wherein n is an integer from 0-20.

14. The compound of claim 13, wherein n is an integer selected from 0-3.

15. The compound of claim 13, wherein n is 0, 1, or 2.

16. The compound of claim 1, wherein the C—O bond of the number 1 carbon atom of each glucoside or glycoside unit is oriented as an alpha-glycosidic linkage.

17. The compound of claim 1, wherein the C—O bond of the number 1 carbon atom of each glucoside or glycoside unit is oriented as a beta-glycosidic linkage.

18. A method of making the compound of claim 1, wherein the method comprises the step of reacting a compound of the Formula A, with a glucose or glucoside compound of Formula B corresponding to the glycone portion of the compound of Formula I, II, or III, in a condensation reaction to form the compound of Formula I, II, or III:

-continued

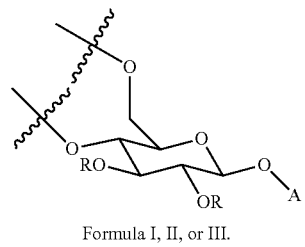

Formula I, II, or III.

wherein substituents A and R, are as defined in claim 1.

19. A method of making the compound of claim 1, wherein the method comprises the step of reacting a compound of the Formula E, with a compound of Formula B in an electrophilic alkene addition reaction to form the compound of Formula I, II, or III, provided that the compound of Formula E is formable by the dehydration of a compound of Formula A:

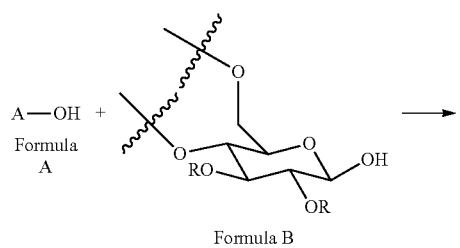

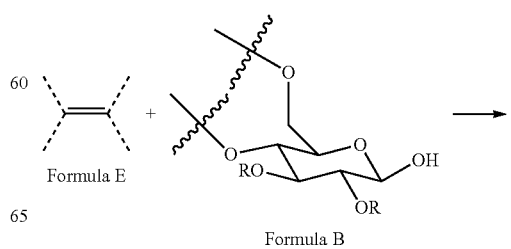

-continued

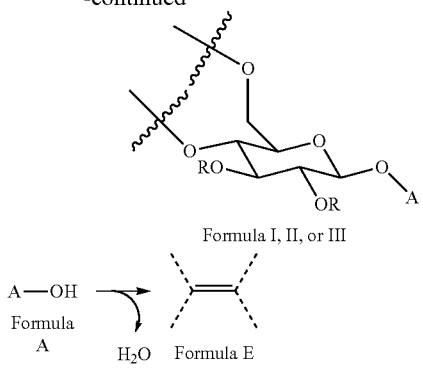

Formula I, II, or III wherein substituents A and R, are as defined in claim 1, and wherein the structure of Formula E is contingent on the structure of Formula A, such that elimination of the OH group and an H atom from adjacent carbon atoms will result in the compound of Formula E.

20. A composition comprising a compound according to claim 1, in admixture with one or more pharmaceutically acceptable, cosmetically acceptable, or industrially acceptable excipients or carriers.

21. The composition of claim 20, wherein the one or more pharmaceutically acceptable, cosmetically acceptable, or industrially acceptable excipients or carriers are selected from the group consisting of solvents, oils, surfactants, emollients, diluents, glidants, abrasives, humectants, polymers, plasticizers, catalysts, antioxidants, coloring agents, flavoring agents, fragrance agents, antiperspirant agents, antibacterial agents, antifungal agents, hydrocarbons, stabilizers, and viscosity controlling agents.

22. A product comprising the compound of claim 1, wherein the product is selected from the group consisting of perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, anti-perspirants, shampoos, colognes, shower gels, hair sprays, and pet litter.

23. A cosmetic or personal care composition comprising the compound of claim 1, wherein the composition is selected from the group consisting of cosmetics, soaps, body washes, skin and hair cleansers, skin creams and lotions, facial creams and lotions, face oils, eye cream, ointments, sunscreens, moisturizers, hair shampoos, hair conditioners, deodorants, antiperspirants, hair sprays, hair styling gel, hair mousse, nail polish, eye liner, mascara, lipstick, foundation, concealer, blush, bronzer, eye shadow, lip liner, lip balm, and dermocosmetics.

* * * * *